United States Patent [19]
Catterall et al.

[11] Patent Number: 6,090,631
[45] Date of Patent: *Jul. 18, 2000

[54] METHODS AND COMPOSITIONS FOR SCREENING FOR PRESYNAPTIC CALCIUM CHANNEL BLOCKERS

[75] Inventors: William A. Catterall; Zu-Hang Sheng, both of Seattle, Wash.

[73] Assignee: University of Washington, Seattle, Wash.

[*] Notice: This patent is subject to a terminal disclaimer.

[21] Appl. No.: 08/558,135

[22] Filed: Nov. 13, 1995

Related U.S. Application Data

[63] Continuation-in-part of application No. 08/337,602, Nov. 10, 1994, Pat. No. 5,623,051.

[51] Int. Cl.[7] .................................................. G01N 33/566
[52] U.S. Cl. ............................................ 436/501; 435/7.8
[58] Field of Search ..................................... 436/501, 503; 514/8, 12, 21; 530/322, 324, 350, 395, 839; 435/7.8

[56] References Cited

U.S. PATENT DOCUMENTS 5,623,051  4/1997  Catterall et al. .

FOREIGN PATENT DOCUMENTS

WO 89/09834  10/1989  WIPO .
WO 91/13077  9/1991  WIPO .
WO 93/04083  3/1993  WIPO .

OTHER PUBLICATIONS

Sheng et al, *Neuron* vol. 13 pp. 1303–1313, Dec. 1994.
Horikawa et al *FEBS Letters* 330(2) p 236–40 Abstract only, Sep. 13, 1993.
George et al, Macromolecular Sequencing and Synthesis selected methods and applications, pp. 127–149, 1998 Alan R. Liss, Inc.
Bennett et al., "Syntaxin: A Synaptic Protein Implicated in Docking of Synaptic Vesicles at Presynaptic Active Zones," *Science* 257:255–259, 1992.
Bennett et al., "The Syntaxin Family of Vesicular Transport Receptors," *Cell* 74:863–873, 1993.
Léveque et al., "Purification of the N–type Calcium Channel Associated with Syntaxin and Synaptotagmin. A Complex Implicated in Synaptic Vesicle Exocytosis," *Journal of Biological Chemistry* 269(9): 6306–6312, 1994.
Westenbroek et al., "Biochemical Properties and Subcellular Distribution of an N–type Calcium Channel α1 Subunit," *Neuron* 9: 1099–1115, 1992.

*Primary Examiner*—Patricia A. Duffy
*Attorney, Agent, or Firm*—Seed Intellectual Property Law Group PLLC

[57] ABSTRACT

Methods and compositions related to the identification of compounds that block neurotransmitter release are disclosed. Using the methods of the present invention, candidate compounds may be screened for the ability to bind to presynaptic calcium channels such that the docking of presynaptic vesicles to presynaptic calcium channels will be inhibited. The present invention also discloses peptides useful in the screening methods.

2 Claims, 19 Drawing Sheets

Fig.11A- 710 Val Asp Asn Leu Ala Asn Ala Gln Glu Leu Thr Lys Asp Glu Glu Glu Met Glu Glu Ala Ala Asn Gln Lys Leu 734
Fig.11B- 710 .   Asp Asn Leu Ala Asn Ala Gln Glu Leu Thr Lys Asp Glu Glu Glu Met Glu Glu Ala Ala Asn Gln Lys Leu 733

735 Ala Leu Gln Lys Ala Lys Glu Val Ala Glu Val Ser Pro Met Ser Ala Ala Asn Ile Ser Ile Ala Ala Arg Gln 759
734 Ala Leu Gln Lys Ala Lys Glu Val Ala Glu Val Ser Pro Met Ser Ala Ala Asn Ile Ser Ile Ala Ala Arg Gln 758

760 Gln Asn Ser Ala Lys Ala Arg Ser Val Trp Glu Gln Arg Ala Ser Gln Leu Arg Leu Gln Asn Leu Arg Ala Ser 784
759 Gln Asn Ser Ala Lys Ala Arg Ser Val Trp Glu Gln Arg Ala Ser Gln Leu Arg Leu Gln Asn Leu Arg Ala Ser 783

785 Cys Glu Ala Leu Tyr Ser Glu Met Asp Pro Glu Glu Arg Leu Arg Tyr Ala Ser Thr Arg His Val Arg Pro Asp 809
784 Cys Glu Ala Leu Tyr Ser Glu Met Asp Pro Glu Glu Arg Leu Arg Phe Ala Thr Thr Arg His Leu Arg Pro Asp 808

810 Met Lys Thr His Met Asp Arg Pro Leu Val Val Glu Pro Gly Arg Asp Gly Leu Arg Gly Pro Ala Gly Asn Lys 834
809 Met Lys Thr His Leu Asp Arg Pro Leu Val Val Glu Leu Gly Arg Asp Gly Ala Arg Gly Pro Val Gly Gly Lys 833

835 Ser Lys Pro Glu Gly Thr Glu Ala Thr Glu Gly Ala Asp Pro Pro Arg Arg His His Arg His Arg Asp Arg Asp 859
834 Ala Arg Pro Glu Ala Ala Glu Ala Pro Glu Gly Val Asp Pro Pro Arg Arg His His Arg His Arg Asp Lys Asp 858

860 Lys Thr Ser Ala Ser Thr Pro Ala Gly Gly Glu Gln Asp Arg Thr Asp Cys Pro Lys Ala Glu Ser Thr Glu Thr 884
859 Lys .   .   .   .   Thr Pro Ala Ala Gly Asp Gln Asp Arg Ala Glu Ala Pro Lys Ala Glu Ser Gly Glu Pro 879

885 Gly Ala Arg Glu Glu Arg Ala Arg Pro Arg Arg Ser His Ser Lys Glu Ala Pro Gly Ala Asp Thr Gln Val Arg 909
880 Gly Ala Arg Glu Glu Arg Pro Arg Pro His Arg Ser His Ser Lys Glu Ala Ala Gly Pro .   Pro Glu Ala Arg 903

910 Cys Glu Arg .   .   .   .   .   .   Ser Arg Arg His His Arg Arg Gly Ser Pro Glu Glu Ala Thr 926
904 Ser Glu Arg Gly Arg Gly Pro Gly Pro Glu Gly Gly Arg Arg His His Arg Arg Gly Ser Pro Glu Glu Ala Ala 928

927 Glu Arg Glu Pro Arg Arg His Arg Ala His Arg His Ala Gln Asp Ser Ser Lys Glu Gly Lys Glu Gly Thr Ala 951
929 Glu Arg Glu Pro Arg Arg His Arg Ala His Arg His .   Gln Asp Pro Ser Lys Glu Cys Ala Gly Ala .   .   950

952 Pro Val Leu Val Pro Lys Gly Glu Arg Arg Ala Arg His Arg .   Gly Pro Arg Thr Gly Pro Arg Glu Thr Glu 975
951 .   .   .   .   .   Lys Gly Glu Arg Arg Ala Arg His Arg Gly Gly Pro Arg Ala Gly Pro Arg Glu Ala Glu 970

976 Asn Ser Glu Glu Pro Thr Arg Arg His Arg Ala Lys His Lys Val Pro Pro Thr Leu Glu Pro .   .   .   .   996
971 Ser Gly Glu Glu Pro Ala Arg Arg His Arg Ala Arg His Lys Ala Gln Pro Ala His Glu Ala Val Glu Lys Glu 995

997 .   Pro Glu Arg Glu Val Ala Glu Lys Glu Ser Asn Val Val Glu Gly Asp Lys Glu Thr .   .   Arg Asn His 1018
996 Thr Thr Glu Lys Glu Ala Thr Glu Lys Glu Ala Glu Ile Val Glu Ala Asp Lys Glu Lys Glu Leu Arg Asn His 1020

1019 Gln Pro Lys Glu Pro Arg Cys Asp Leu Glu Ala Ile Ala Val Thr Gly Val Gly Ser Leu His Met Leu Pro Ser 1043
1021 Gln Pro Arg Glu Pro His Cys Asp Leu Glu Thr Ser Gly Thr Val Thr Val Gly Pro Met His Thr Leu Pro Ser 1045

1044 Thr Cys Leu Gln Lys Val Asp Glu Gln Pro Glu Asp Ala Asp Asn Gln Arg Asn Val Thr Arg Met Gly Ser Gln 1068
1046 Thr Cys Leu Gln Lys Val Glu Glu Gln Pro Glu Asp Ala Asp Asn Gln Arg Asn Val Thr Arg Met Gly Ser Gln 1070

1069 Pro Ser Asp Pro Ser Thr Thr Val His Val Pro Val Thr Leu Thr Gly Pro Gly Glu Ala Thr Val Val Pro 1093
1071 Pro Pro Asp Pro Asn Thr Ile Val His Ile Pro Val Met Leu Thr Gly Pro Leu Gly Ala Thr Val Val Pro 1095

1094 Ser Ala Asn Thr Asp Leu Glu Gly Gln Ala Glu Gly Lys Lys Glu Ala Glu Ala Asp Asp Val Leu Arg Arg Gly 1118
1096 Ser Gly Asn Val Asp Leu Glu Ser Gln Ala Glu Gly Lys Lys Glu Val Glu Ala Asp Asp Val Met Arg Ser Gly 1120

1119 Pro Arg Pro Ile Val Pro Tyr Ser Ser Met Phe Cys Leu Ser Pro Thr Asn Leu Leu Arg Arg Phe Cys His Tyr 1143
1121 Pro Arg Pro Ile Val Pro Tyr Ser Ser Met Phe Cys Leu Ser Pro Thr Asn Leu Leu Arg Arg Phe Cys .   .   1143

```
  1  Met Lys Asp Arg Thr Gln Glu Leu Arg Thr Ala Lys Asp Ser Asp Asp Asp Val Thr Val Asp
 26  Arg Asp Arg Phe Met Asp Glu Phe Phe Glu Gln Val Glu Glu Ile Arg Gly Phe Ile Asp Lys Ile Ala Glu Asn
 51  Val Glu Glu Val Lys Arg Lys His Ser Ala Ile Leu Ala Ser Pro Asn Pro Asp Glu Lys Thr Lys Glu Glu Leu
 76  Glu Glu Leu Met Ser Asp Ile Lys Lys Ala Asn Lys Val Arg Ser Leu Lys Ser Ile Glu Gln Ser Ile
101  Glu Gln Glu Gly Leu Asn Arg Ser Ser Ala Asp Leu Arg Ile Arg Lys Thr Gln His Ser Thr Leu Ser Arg
126  Lys Phe Val Glu Val Met Ser Glu Tyr Asn Ala Thr Gln Ser Asp Tyr Arg Glu Arg Cys Lys Gly Arg Ile Gln
151  Arg Gln Leu Glu Ile Thr Gly Arg Thr Thr Ser Glu Leu Glu Asp Met Leu Glu Ser Gly Asn Pro Ala
176  Ile Phe Ala Ser Gly Ile Ile Met Asp Ser Ser Ile Ser Gln Ala Leu Ser Glu Ile Glu Thr Arg His Ser
201  Glu Ile Ile Lys Leu Glu Asn Ser Ile Arg Glu Leu His Asp Met Phe Met Asp Met Ala Met Leu Val Glu Ser
226  Gln Gly Met Ile Asp Arg Ile Glu Tyr Asn Val Glu His Ala Val Asp Tyr Val Glu Arg Ala Val Ser Asp
251  Thr Lys Lys Ala Val Lys Tyr Gln Ser Lys Ala Arg Arg Lys Lys Ile Met Ile Ile Cys Cys Val Ile Leu
276  Gly Ile Ile Ile Ala Ser Thr Ile Gly Gly Ile Phe Gly
```

*Figure 12*

↓722
ELTKDEQEEEEAvNQKLALQKAKEVAEVSPLSAANMSIAmKEQQKNQKPAKSVWEQRTSEMRKQNL
ELTKDEQEEEEAANQKLALQKAKEVAEVSPLSAANMSIAVKEQQKNQKPAKSVWEQRTSEMRKQNL
ELTKDEQEEEEAANQKLALQKAKEVAEVSPLSAANMSIAVKEQQKNQKPAKSVWEQRTSEMRKQNL
↑724                                                      ↓843

LASREALYsEMDPeERWKAsYARHLRPDMKTHLDRPLVVDPQENRNNNTNKSRvAEPTVDQRLGQQ
LASREALYnEMDPdERWKAaYtRHLRPDMKTHLDRPLVVDPQENRNNNTNKSRAAEPTVDQRLGQQ
LASREALYg--DaaERWpttYARpLRPDvKTHLDRPLVVDPQENRNNNTNKSRApEa-------
                                                    ↑844
                                         ↓895
RAEDFLRKQARhHDRARDPSahAaaGLDARRPWAGSQEAELSREGPYGRESDHQAREGgLEPPGF-
RAEDFLRKQARyHDRARDPSgsA--GLDARRPWAGSQEAELSREGPYGRESDHhAREGsLEqPGF-
----LRqtARpresARDP-------DARRaWpsSpErapgREGPYGRESepQqREha--PPreh
                                         ↑869

---WEGEAERGKAGDPHRRHaHRQGvgGSsgSRSGgSRSGSPRTGtADGEPRRHRvHRRPGEdGPDDKAERR
---WEGEAERGKAGDPHRRHVHRQG--GSreSRSGSPRTG-ADGEhRRHRAHRRPGEEGPeDKAERR
vpWdadpERaKAGDapRRHtHRpv---------------AeGEPRRHRArRRPGdE-PDDrpERR
                                                  ↓1036
gRHREGSRPARsGEGEaEGPDGGggggERRRRHGPPpaYdpDARRDDRERR
aRHREGSRPARgGEGEgEGPDGG----ERRRRHRHGaPATYegDARReDkERR
pRpRdatRPARaadGE--GdDG-----ErKrRHRHGPPAh-------DDRERR
                                        ↑981

*Figure 15*

METHODS AND COMPOSITIONS FOR SCREENING FOR PRESYNAPTIC CALCIUM CHANNEL BLOCKERS

This application is a continuation-in-part of U.S. patent application Ser. No. 08/337,602, filed Nov. 10, 1994, now U.S. Pat. No. 5,623,051.

This invention was made with government support under grant number NS 22625 awarded by the National Institutes of Health. The government has certain rights in the invention.

TECHNICAL FIELD

The present invention is generally directed toward assays and compositions for identifying compounds that block neurotransmitter release. This invention is more particularly related to screening candidate compounds for the ability to block presynaptic calcium channels.

BACKGROUND OF THE INVENTION

The release of neurotransmitters from presynaptic terminals is the final response of a nerve to the excitatory and inhibitory inputs that converge upon it. Neurotransmitter release at the presynaptic terminal of neurons is primarily initiated by the entry of calcium through voltage-gated calcium channels (Smith and Augustine, *Trends Neurosci.* 11:458–464, 1988; Robitaille et al., *Neuron* 5:773–779, 1990). Exocytosis of synaptic vesicles occurs at specialized regions of the nerve terminal called active zones. These zones may contain clusters of presynaptic calcium channels that supply calcium for neurotransmitter release (Pumplin et al., *Proc. Natl. Acad. Sci. USA* 78:7210–7214, 1981; Pumplin, *J. Neurocytol.* 12:317–323, 1983; Zucker, *J. Physiol.* 87:25–36, 1993). The entry of calcium through voltage-gated calcium channels couples electrical activity to secretion of synaptic vesicles. Synaptic transmission is initiated within 200 μs after the arrival of the action potential at the synaptic terminal. The brief rise in $Ca^{++}$ concentration to the level necessary for exocytosis likely occurs only in proximity to the calcium channels (Llinás et al., *Biophys. J.* 33:289–322; Cope and Mendell, *J. Neurosci.* 47:469–478, 1982).

A combination of electrophysiological and pharmacological criteria have defined four main types of high-voltage-activated calcium channels that are widely distributed in mammalian neurons. These are ω-conotoxin-GVIA-sensitive N-type calcium channels, ω-agatoxin IVA-sensitive and ω-conotoxin-MVIIC-sensitive P-type and Q-type calcium channels, and dihydropyridine-sensitive L-type calcium channels (for reviews see Bean, *Annu. Rev. Physiol.* 51:367–384, 1989; Hess, *Ann. Rev. Neurosci.* 13:337–356, 1990; Tsien et al., *Trends Pharmac. Sci.* 12:349–354, 1991; Miller, *J. Biol. Chem.* 267:1403–1406, 1992; Zhang et al., *Neuropharmacology* 32:1075–1088, 1993). Several lines of evidence indicate that N-type channels, at least in part, are responsible for the calcium influx that triggers transmitter release in many neurons. Antibodies against ω-conotoxin GVIA (ω-CTx GVIA) or fluorescent toxin derivatives label active zones on the terminals of motor neurons at the frog neuromuscular junction (Robitaille et al., *Neuron* 5:773–779, 1990; Cohen et al., *J. Neurosci* 1:1032–1039, 1991). Immunocytochemical studies with specific site-directed anti-peptide antibodies indicate that N-type channels are located along the length of dendrites and in synapses formed on the dendrites of many brain neurons (Westenbroek et al., *Neuron* 9:1099–1115, 1992). In contrast, antibodies to L-type channels recognize calcium channels in cell bodies and proximal dendrites, but give no detectable staining of presynaptic terminals in brain (Ahlijanian et al., *Neuron* 4:819–832, 1990). In addition, ω-CTx-GVIA inhibits transmitter release in a variety of mammalian neuronal preparations (Hirning et al., *Science* 239:57–60, 1988; Horne and Kemp, *Br. J. Pharmacol.* 103:1733–1739, 1991; Takahashi and Momiyama, *Nature* 366:156–158, 1993; Luebke et al., *Neuron* 11:895–902, 1993; Turner et al., *Proc. Natl. Acad. Sci. USA* 90:9518–9522, 1993; Wheeler et al., *Science* 264:107–111, 1994), thus supporting the hypothesis that N-type channels play a role in controlling neurotransmitter release in the central nervous system. Similarly, P-type and Q-type channels (collectively P/Q-type channels) have been implicated in neurotransmitter release in mammalian neurons. N-type channels appear to be the dominant form in presynaptic terminals of the peripheral nervous system, and P/Q-type channels in presynaptic terminals of the central nervous system.

Molecular cloning has identified the primary structures of the main pore-forming α1 subunit of five distinct classes of calcium channels (classes A, B, C, D, and E) found in rat brain. Cloned neuronal $α1_C$ and $α1_D$ subunits are components of L-type channels, while the $α1_B$ subunit is a component of N-type channels (Dubel et al., *Proc. Natl. Acad. Sci. USA* 89:5058–5062, 1992; Williams et al., *Neuron* 8:71–84, 1992a; Williams et al., *Science* 257:389–395, 1992b; Westenbroek et al., *Neuron* 9:1099–1115, 1992; Stea et al., *Neuropharmacology* 32:1103–1116, 1993). $α1_A$ encodes Q-type calcium channels and may also encode P-type calcium channels (Snutch and Reiner, *Curr. Opin. Neurobiol.* 2:247–253, 1992; Tsien etal., *Trends Pharmac. Sci.* 12:349–354, 1991; Mori et al., *Nature* 350:398–402, 1991; Sather et al., *Neuron* 11:291–303, 1993; Zhang et al., *Neuropharmacology* 32:1075–1088, 1993). The deduced amino acid sequence of $α1_B$ shares overall structural features with other calcium channel α1 subunits. It is composed of four predominantly hydrophobic homologous domains (I–IV) that are linked by intracellular hydrophilic loops of various lengths.

The traditional approach to blocking neurotransmitter release has been to use compounds that bind to the neuronal voltage-gated calcium channels in a manner such that calcium entry through the channels is blocked. One of the difficulties in such an approach is the lack of specificity. As noted above, voltage-activated calcium channels that are found at sites in the body other than at presynaptic terminals appear to share structural features responsible for the movement of calcium through the channels. Accordingly, compounds that interact with the pore portion of calcium channels to block calcium entry into presynaptic nerve terminals will also block calcium channels at other sites throughout the body. Therefore, the traditional compounds for blocking neurotransmitter release have undesired side effects due to the blockade of additional calcium channels.

Due to the limited success for previously suggested compounds for the inhibition of neurotransmitter release, there is a need in the art for methods and compositions to screen for new inhibitors with specificity for presynaptic voltage-gated calcium channels. The present invention fulfills this need, and further provides other related advantages.

SUMMARY OF THE INVENTION

Current compounds in the art for blocking neurotransmitter release act by inhibiting the calcium influx through calcium channels that triggers transmitter release. As noted above, this approach suffers from problems associated with the inhibition of calcium channels at sites other than presynaptic terminals of neurons. An advantage of the methods and compositions of the present invention is that compounds are screened for the ability to inhibit the docking of presynaptic vesicles to presynaptic calcium channels, rather than for the ability to inhibit calcium influx through the channels.

Briefly stated, the present invention provides a variety of methods and compositions related to screening compounds for the ability to inhibit the interaction between presynaptic calcium channels and presynaptic vesicles (e.g., by a compound's ability to bind to a selected presynaptic calcium channel-like peptide). In one aspect, the present invention provides methods of screening for compounds that inhibit the interaction between presynaptic calcium channels and presynaptic vesicles. In one embodiment, the method comprises the steps of: (a) contacting a calcium channel-like peptide with a candidate compound under conditions sufficient to permit binding between the peptide and the candidate compound, wherein the peptide is able to bind syntaxin or SNAP-25; and (b) detecting the presence or absence of binding between the peptide and the candidate compound, thereby determining whether the candidate compound bound to the peptide.

In another embodiment of the method, step (a) further includes syntaxin or a syntaxin-like peptide under conditions sufficient to permit binding between the calcium channel-like peptide and the syntaxin or the syntaxin-like peptide; and step (b) comprises detecting the presence or absence of binding between the calcium channel-like peptide and the syntaxin or the syntaxin-like peptide, thereby determining whether the candidate compound inhibited the binding.

In another embodiment of the method, step (b) comprises the steps of: (b) adding syntaxin or a syntaxin-like peptide to the reaction mixture of the candidate compound and the calcium channel-like peptide of step (a) under conditions sufficient to permit binding between the calcium channel-like peptide and the syntaxin or the syntaxin-like peptide, and (c) detecting the presence or absence of binding between the calcium channel-like peptide and the syntaxin or the syntaxin-like peptide, thereby determining whether the candidate compound inhibited the binding.

In another embodiment of the method, step (a) further includes SNAP-25 or a SNAP-25-like peptide under conditions sufficient to permit binding between the calcium channel-like peptide and the SNAP-25 or the SNAP-25-like peptide; and step (b) comprises detecting the presence or absence of binding between the calcium channel-like peptide and the SNAP-25 or the SNAP-25-like peptide, thereby determining whether the candidate compound inhibited the binding.

In another embodiment of the method, step (b) comprises the steps of: (b) adding SNAP-25 or a SNAP-25-like peptide to the reaction mixture of the candidate compound and the calcium channel-like peptide of step (a) under conditions sufficient to permit binding between the calcium channel-like peptide and the SNAP-25 or the SNAP-25-like peptide, and (c) detecting the presence or absence of binding between the calcium channel-like peptide and the SNAP-25 or the SNAP-25-like peptide, thereby determining whether the candidate compound inhibited the binding.

In any of the above embodiments, the calcium channel-like peptide may be such that it has at least 87 amino acid residues selected from amino acid 717 to amino acid 1143 of an $\alpha_1$ subunit of a N-type or Q-type calcium channel. The 87 or more amino acids are sequential.

In a related aspect, the present invention provides peptides derived from, or based upon, a selected portion of a presynaptic calcium channel amino acid sequence. In one embodiment, the peptide consists of the amino acid sequence of FIG. 11A (SEQ ID NO: 2) from alanine, amino acid 773, to aspartic acid, amino acid 859. In another embodiment, the peptide consists of the amino acid sequence of FIG. 11A (SEQ ID NO: 2) from glutamic acid, amino acid 718, to aspartic acid, amino acid 859. In another embodiment, the peptide consists of the amino acid sequence of FIG. 11A (SEQ ID NO: 2) from glutamic acid, amino acid 718, to arginine, amino acid 963. In another embodiment, the peptide consists of the amino acid sequence of FIG. 11A (SEQ ID NO: 2) from glutamic acid, amino acid 718, to cysteine, amino acid 1141. In another embodiment, the peptide consists of the amino acid sequence of FIG. 11A (SEQ ID NO: 2) from an amino acid positioned between glutamic acid, amino acid 718, and alanine, amino acid 773, to an amino acid positioned between aspartic acid, amino acid 859, and cysteine, amino acid 1141. In another embodiment, the peptide consists of an amino acid sequence of between 246 to 424 amino acid residues in length, wherein the amino acid sequence contains an amino acid sequence having at least 60% sequence similarity with the amino acid sequence of FIG. 11A (SEQ ID NO: 2) from glutamic acid, amino acid 718, to arginine, amino acid 963.

In another embodiment, the peptide consists of the amino acid sequence of FIG. 11B (SEQ ID NO: 3) from alanine, amino acid 772, to aspartic acid, amino acid 858. In another embodiment, the peptide consists of the amino acid sequence of FIG. 11B (SEQ ID NO: 3) from glutamic acid, amino acid 717, to aspartic acid, amino acid 858. In another embodiment, the peptide consists of the amino acid sequence of FIG. 11B (SEQ ID NO: 3) from glutamic acid, amino acid 717, to threonine, amino acid 1036. In another embodiment, the peptide consists of the amino acid sequence of FIG. 11B (SEQ ID NO: 3) from glutamic acid, amino acid 717, to cysteine, amino acid 1143. In another embodiment, the peptide consists of the amino acid sequence of FIG. 11B (SEQ ID NO: 3) from an amino acid positioned between glutamic acid, amino acid 717, and alanine, amino acid 772, to an amino acid positioned between aspartic acid, amino acid 858, and cysteine, amino acid 1143. In another embodiment, the peptide consists of an amino acid sequence of between 246 to 427 amino acid residues in length, wherein the amino acid sequence contains an amino acid sequence having at least 60% sequence similarity with the amino acid sequence of FIG. 11B (SEQ ID NO: 3) from glutamic acid, amino acid 717, to arginine, amino acid 962.

In yet another embodiment, the peptide consists of the amino acid sequence of hBI of FIG. 15 from glutamic acid, amino acid 722, to arginine, amino acid 1036.

In another aspect, a syntaxin-like peptide is provided and consists of the amino acid sequence of FIG. 12 from isoleucine, amino acid 181, to glycine, amino acid 288.

In another related aspect of the present invention, the particular peptides described above are utilized in methods of screening for compounds that inhibit the interaction between presynaptic calcium channel and presynaptic vesicles. In one embodiment, the method comprises the step of: (a) contacting a presynaptic calcium channel-like peptide as described above with a candidate compound under conditions sufficient to permit binding between the peptide and the candidate compound, and (b) detecting the presence or absence of binding between the peptide and the candidate compound, thereby determining whether the candidate compound bound to the peptide.

In another embodiment, the method comprises the steps of: (a) incubating a candidate compound, a presynaptic calcium channel-like first peptide as described above, and syntaxin or a syntaxin-like second peptide under conditions sufficient to permit binding between the first peptide and syntaxin or between the first peptide and the second peptide, and (b) detecting the presence or absence of binding between the first peptide and syntaxin or between the first peptide and the second peptide, thereby determining whether the candidate compound inhibited the binding.

In another embodiment, the method comprises the steps of: (a) incubating a presynaptic calcium channel-like first peptide as described above and a candidate compound under conditions sufficient to permit binding between the peptide and the candidate compound, to form a reaction mixture, (b) contacting syntaxin or a syntaxin-like second peptide with the reaction mixture under conditions sufficient to permit binding between the first peptide and syntaxin or between the first peptide and the second peptide, and (c) detecting the presence or absence of binding between the first peptide and syntaxin or between the first peptide and the second peptide, thereby determining whether the candidate compound inhibited the binding.

In another embodiment, the method comprises the steps of: (a) incubating a candidate compound, a presynaptic calcium channel-like first peptide as described above, and SNAP-25 or a SNAP-25-like peptide under conditions sufficient to permit binding between the first peptide and SNAP-25 or between the first peptide and the SNAP-25-like peptide, and (b) detecting the presence or absence of binding between the first peptide and SNAP-25 or between the first peptide and the SNAP-25-like peptide, thereby determining whether the candidate compound inhibited the binding.

In yet another embodiment, the method comprises the steps of: (a) incubating a presynaptic calcium channel-like first peptide as described above and a candidate compound under conditions sufficient to permit binding between the peptide and the candidate compound, to form a reaction mixture, (b) contacting SNAP-25 or a SNAP-25-like peptide with the reaction mixture under conditions sufficient to permit binding between the first peptide and SNAP-25 or between the first peptide and the SNAP-25-like peptide, and (c) detecting the presence or absence of binding between the first peptide and SNAP-25 or between the first peptide and the SNAP-25-like peptide, thereby determining whether the candidate compound inhibited the binding.

These and other aspects of the present invention will become evident upon reference to the following detailed description and attached drawings.

BRIEF DESCRIPTION OF THE DRAWINGS

The graph in panel FIG. 10B shows the direct interaction of $^{125}I$-ω-CTx-GVIA receptor and GST-syntaxin. Equal amounts (cpm) of $[^{125}I]$-ω-CTx-GVIA-labeled N-type calcium channels were incubated with affinity matrices containing GST-syntaxin or GST for 3 hr. The beads were washed for three times with PBS, and the amount of bound receptors was assessed by direct counting. The counts from three independent binding data were averaged.

Figure 10A:
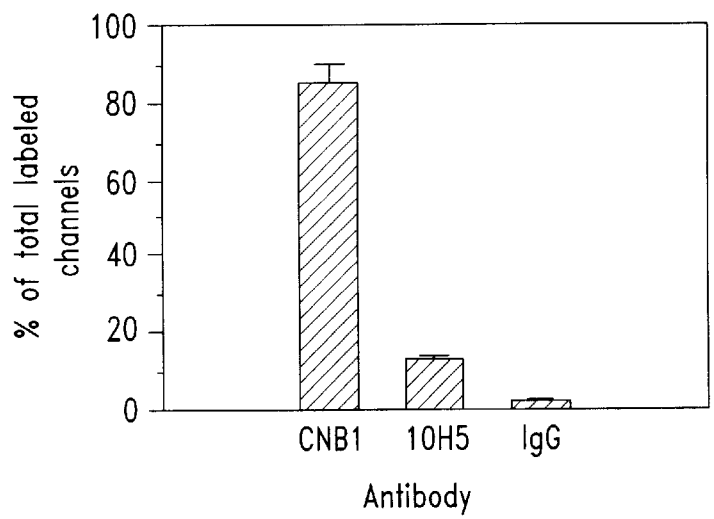
FIGS. 10A, 10B and 10C contain graphs demonstrating the inhibition of N-type calcium channel binding to syntaxin 1A by the 87 amino acid binding peptide. The graph in FIG. 10A shows the extent of immunoprecipitation of $\alpha1_B$ and $\alpha1_B$-syntaxin complex. The class B N-type calcium channels in synaptic membranes were solubilized with digitonin and partially purified by wheat germ agglutinin (WGA)-Sepharose affinity chromatography. The calcium channels were labeled with 500 fmol $[^{125}I]Tyr^{22}$-ω-CTx-GVIA and immunoprecipitated with CNB1 (anti-$\alpha1_B$), 10H5 (anti-syntaxin), and control mouse IgG as indicated. The immunoprecipitation data are expressed as a percentage of the total labeled channels.
Figure 10B:
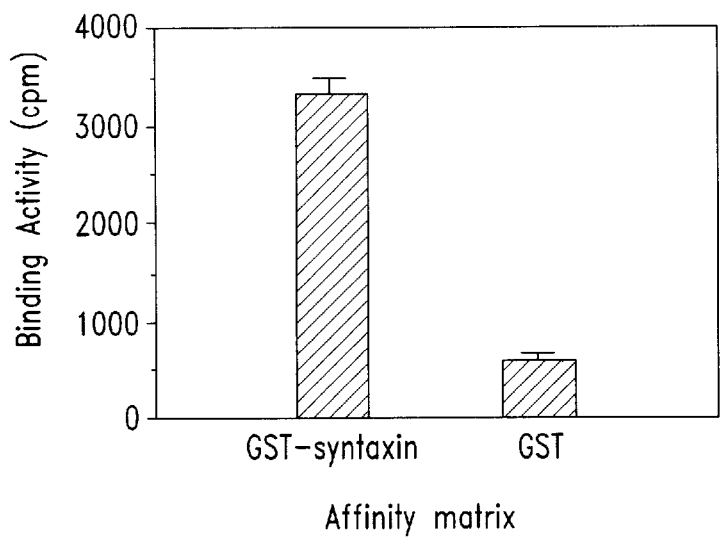
Figure 10C:
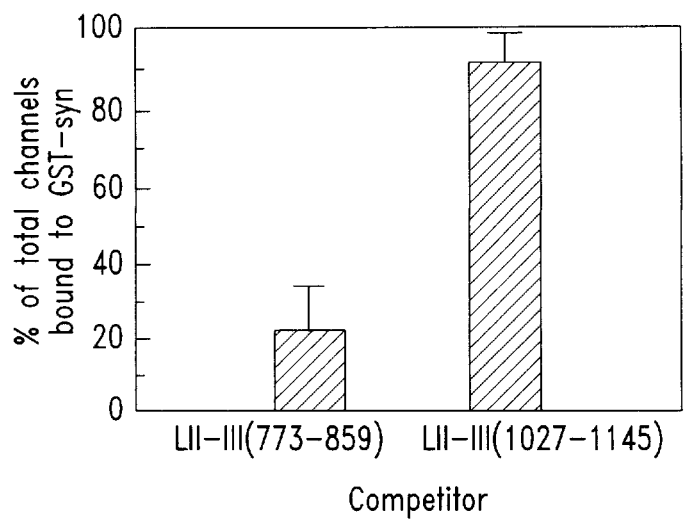

The graph in FIG. 10C displays results of binding competition assays. The binding assays were performed as in FIG. 10B except that the competing peptides, His-$L_{II-III}$ (733–859) or His-$L_{II-III}$(1027–1145) were present. The reduction of binding activity was expressed as a percentage of total binding of labeled receptors to GST-syntaxin in the absence of any competing peptide. The data were averaged from three independent experiments.

FIGS. 11A and 11B show an alignment of loop $L_{II-III}$ (710–1143) amino acid sequences of rat (FIG. 11A (SEQ ID NO: 2) and human (FIG. 11B (SEQ ID NO: 3)) N-type calcium channels. The sequences have been aligned to maximize the sequence similarity.

FIG. 12 depicts the entire amino acid sequence (1–288) of rat syntaxin 1A (SEQ ID NO: 4).

Figure 13:
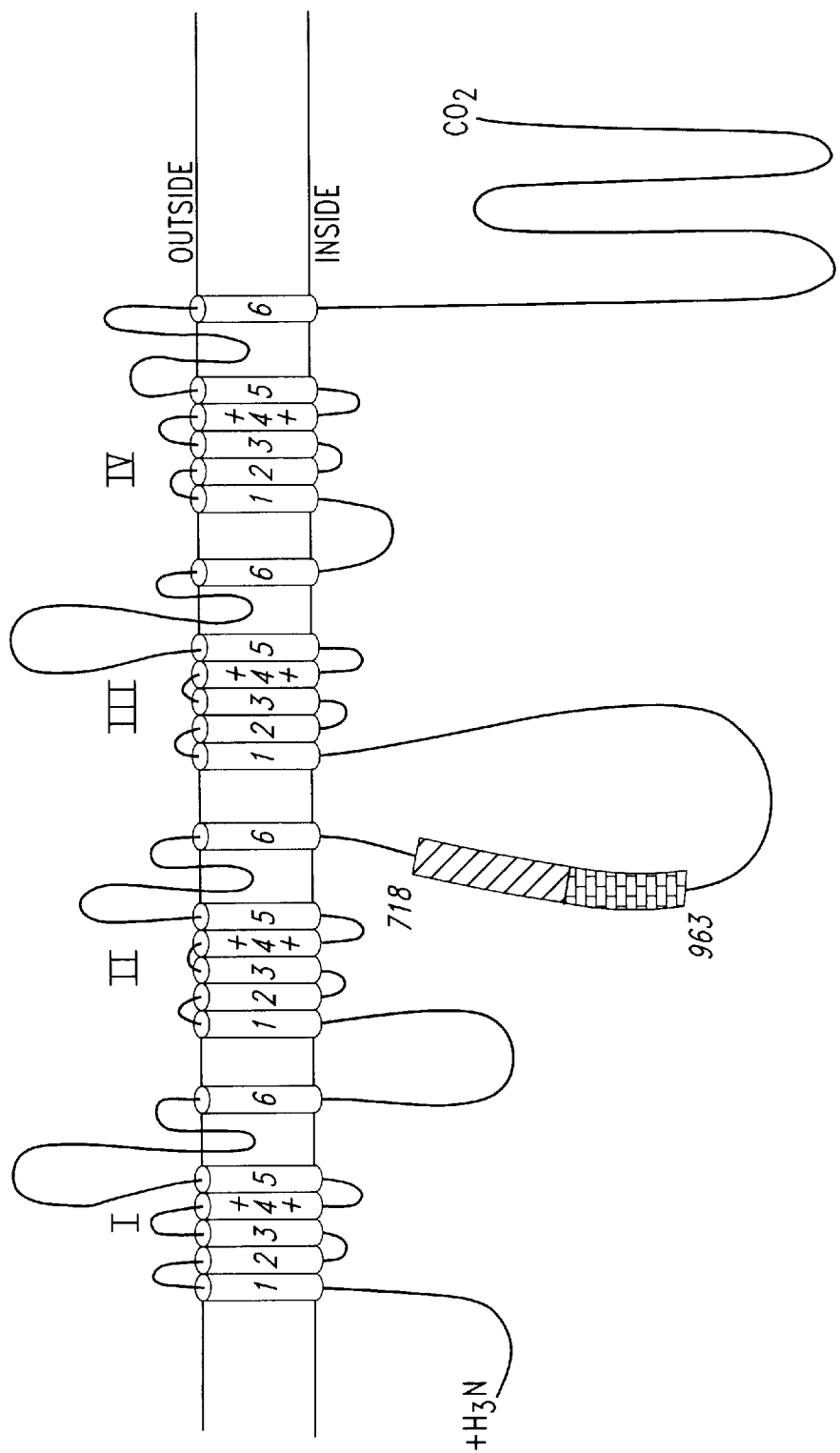

FIG. 13 is a drawing depicting the predicted topological structure of the α1 subunit of the N-type $Ca^{++}$ channel. It is composed of four predominantly hydrophobic homologous domains (I–IV) that are linked by intracellular hydrophilic loops of various lengths. The two syntaxin binding regions in the intracellular loop II are highlighted by shaded boxes.

Figure 14:
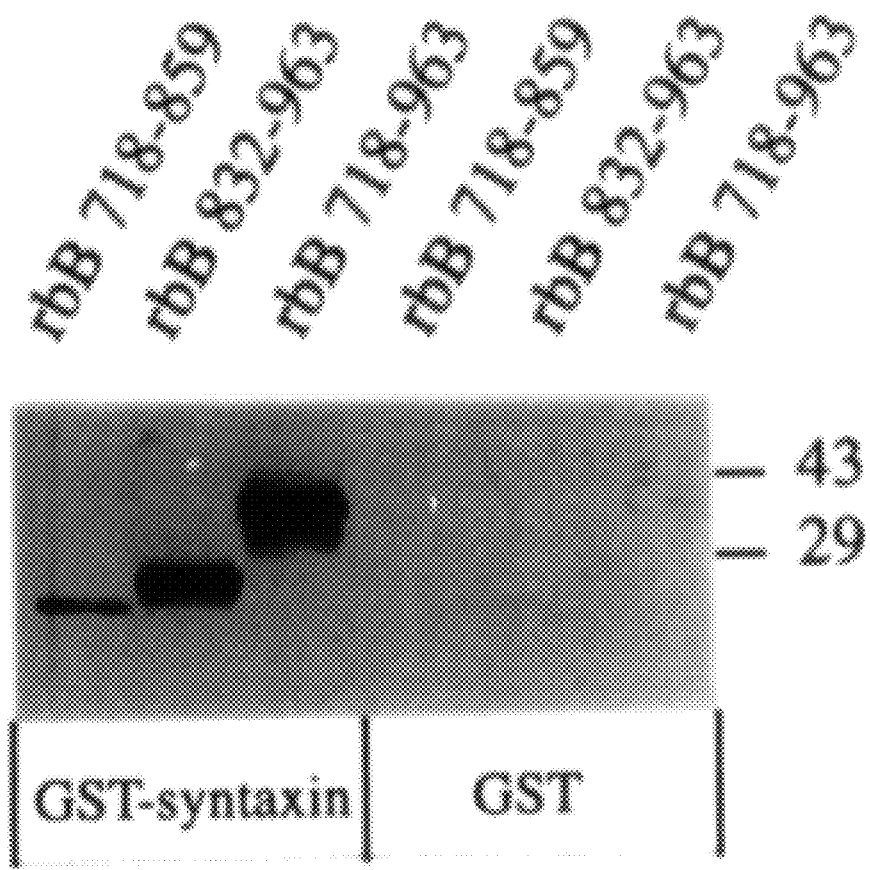

FIG. 14 shows that syntaxin-binding affinity of N-type $Ca^{++}$ channel fusion proteins increases with size. Equal concentrations of GST-syntaxin 1A (5 μM, left lanes) and GST (5 μM, right lanes) were bound to glutathione-Sepharose beads and incubated with various fusion proteins of $L_{II-III}$ of N-type $Ca^{++}$ channels (aa 718–859, 832–963 and 718–963; 10 μM each). The beads were washed and bound proteins were eluted with 15 mM reduced glutathione/50 mM Tris-HCl pH 8. Following SDS-PAGE and electrotransfer to nitrocellulose, the $Ca^{++}$ channel fusion proteins were detected with Anti-T7.Tag monoclonal antibody. Numbers on the right indicate positions of molecular weight markers (in kd). To demonstrate equal concentrations of GST fusion proteins loaded on the beads, Ponceau S staining of the nitrocellulose membrane is shown in the lower panel.

FIG. 15 depicts an alignment of the primary structures of the syntaxin-binding segments of the rbA and BI isoforms of $\alpha_{1A}$. Amino acids are represented by the corresponding one-letter abbreviation, with sequence differences depicted by use of the lower case letter. cDNAs encoding a human BI isoform of the $\alpha_{1A}$ subunit were isolated from a small cell carcinoma line and from human hippocampus and sequenced as described below. The sequences of the rabbit BI isoform of $\alpha_{1A}$ (SEQ ID NO: 5) (Mori et al., Nature 350:398–402, 1991), the rat rbA isoform Of $\alpha_{1A}$ (SEQ ID NO: 7) (Starr et al., Proc. Natl. Acad. Sci. USA 88:5621–5625, 1991), and the human hBI isoform of $\alpha_{1A}$ (SEQ ID NO: 6) are compared, and the positions of the N- and C-termini of the fusion proteins used in these experiments are noted by arrows.

Figure 16:
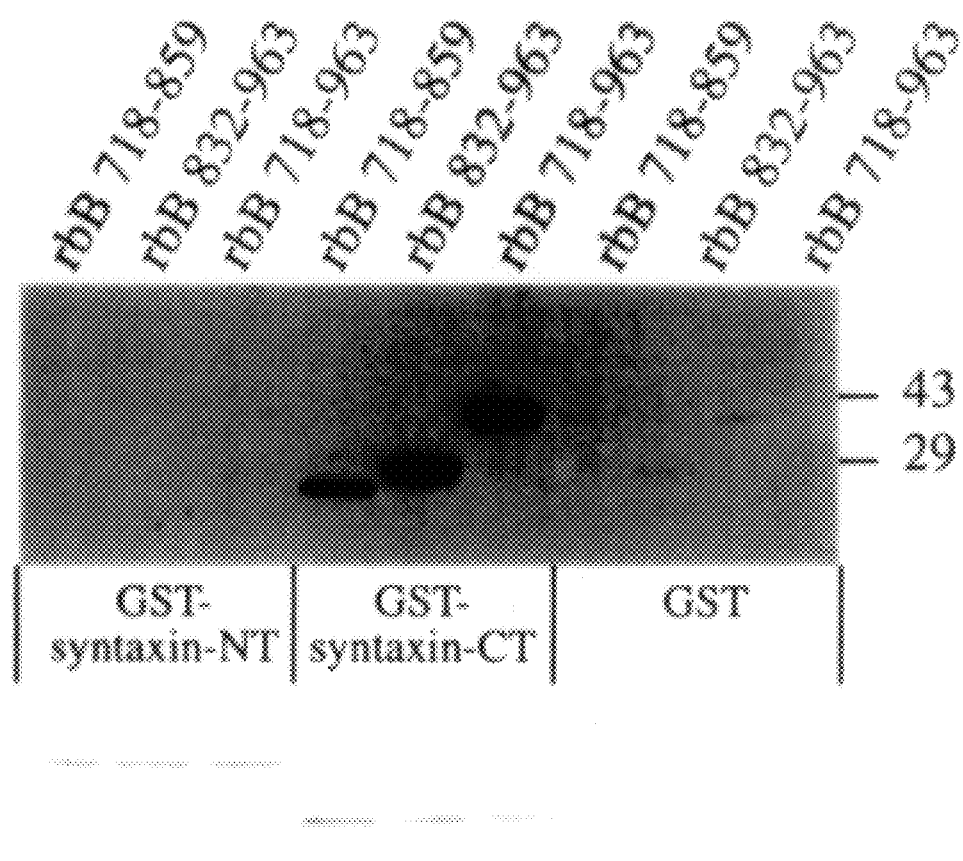

FIG. 16 shows that $\alpha_{1B}$ and the hBI isoform of $\alpha_{1A}$ bind to the C-terminal region of syntaxin 1A. Fusion proteins containing aa 2–190 (N-terminus, lanes 1–3) and aa 181–288 (C-terminus, lanes 4–6) of Syntaxin 1A and GST (lanes 7–9) were bound to glutathione-Sepharose beads. Following a brief wash, beads were incubated with 10 μM of the indicated fusion proteins from $\alpha_{1B}$ (rbB) (A) and hBI (B), respectively. Bound material was fractioned by SDS-PAGE and visualized by immunoblotting.

Figure 17:
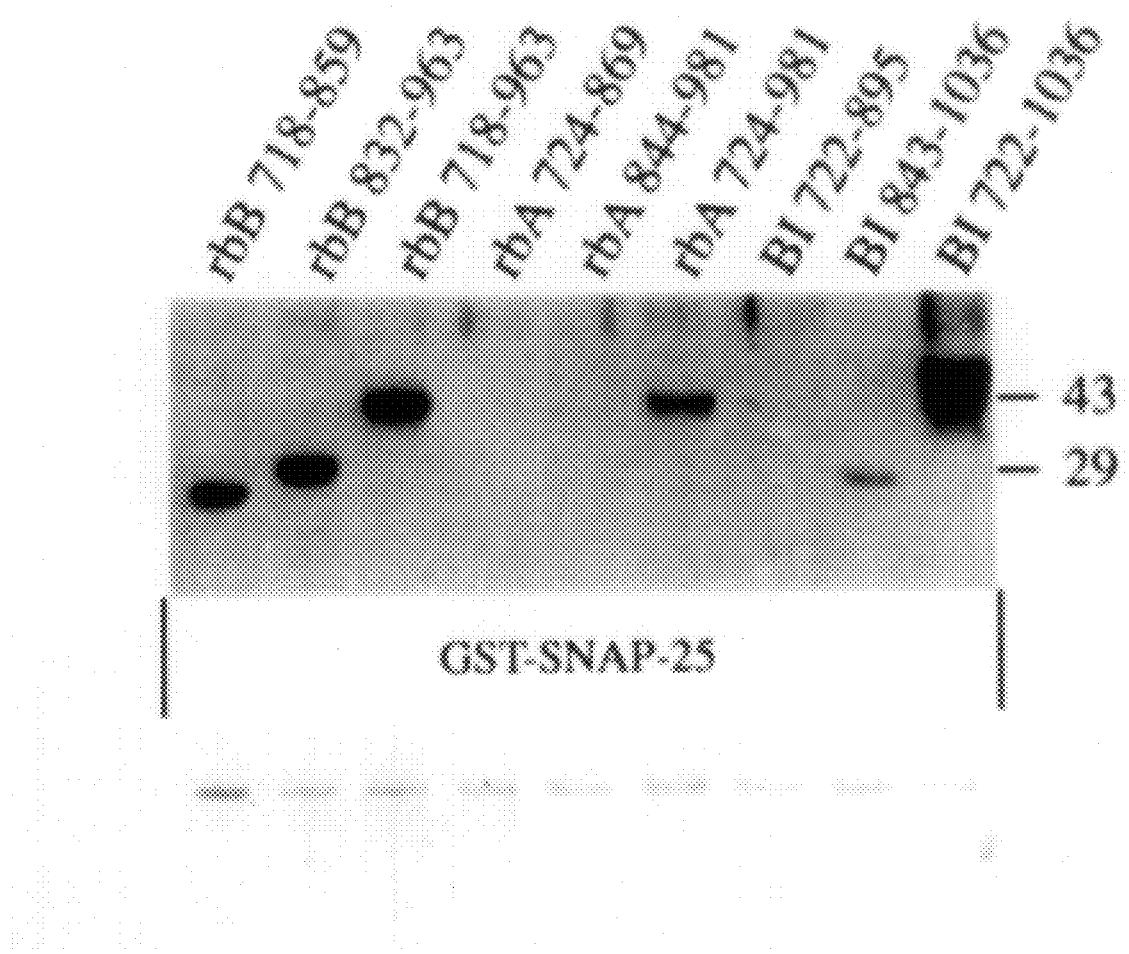

FIG. 17 shows that $\alpha_{1A}$ and $\alpha_{1B}$ bind to the presynaptic protein SNAP-25. GST-SNAP-25 beads (5 μM) were incubated with equal concentrations of various fusion proteins containing $L_{II-III}$ of rbB and the rbA and hBI isoforms of $\alpha_{1A}$ as indicated. Bound material was fractioned by SDS-PAGE and visualized by immunoblotting. Note that the blot is overexposed in order to demonstrate weak binding of both rbA 724–981 and hBI 843–1036. Ponceau S staining of the nitrocellulose membrane is shown below; numbers on the right indicate positions of molecular mass markers (in kDa).

Figure 18:
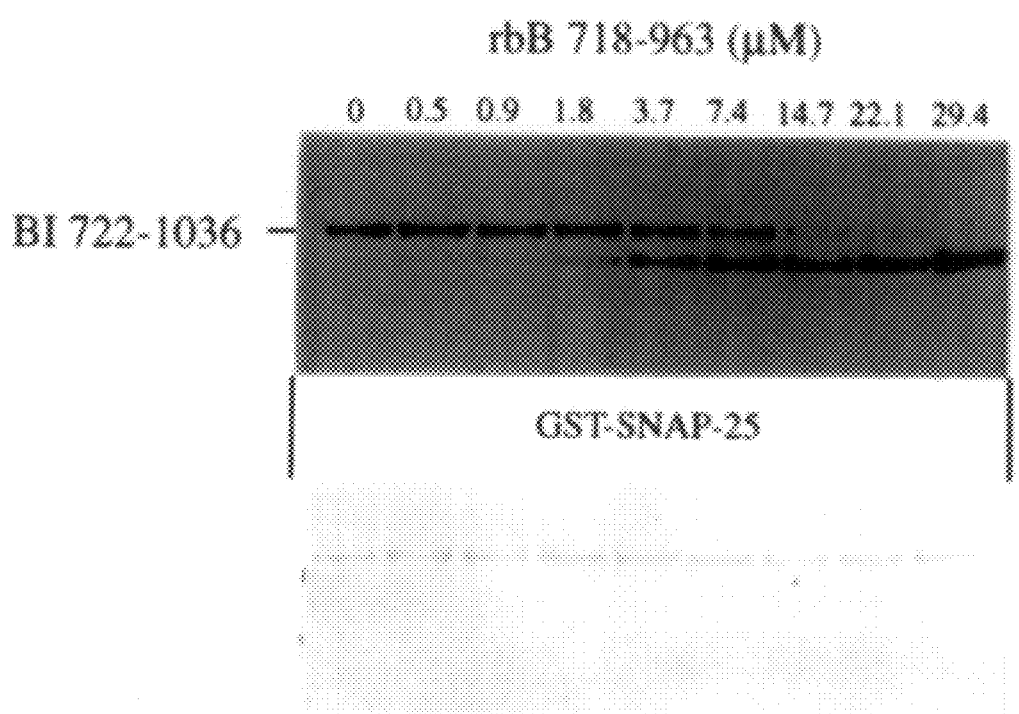

FIG. 18 shows that $\alpha_{1A}$ and $\alpha_{1B}$ compete for the same binding region on SNAP-25. GST-SNAP-25 beads (5 μM) were incubated with equal concentrations of hBI 722–1036 and increasing concentrations of rbB 718–963 as indicated. Bound material was fractioned by SDS-PAGE and visualized by immunoblotting as described below. Ponceau S staining of the nitrocellulose membrane is shown in the lower panels.

DETAILED DESCRIPTION OF THE INVENTION

The identification of calcium channel blockers that specifically inhibit the presynaptic calcium channels involved in release of neurotransmitters, such as glutamate, at excitatory synapses in the central nervous system would be therapeutically beneficial (e.g., in preventing the neuronal cell death that accompanies cerebral ischemia). As described above, compounds that block the calcium conductance activity of these channels are not specific. The present invention provides a screening approach, for compounds which prevent neurotransmitter release triggered by presynaptic calcium channels, that is based on inhibition of the docking of presynaptic vesicles to active zones containing the presynaptic calcium channels.

The disclosure of the present invention shows that presynaptic calcium channels possess a site for binding syntaxin and SNAP-25, proteins anchored in the presynaptic plasma membrane, and that this site has a number of uses, including to screen for compounds that block neurotransmitter release. A compound that inhibits syntaxin or SNAP-25 binding to the site (e.g., by the compound occupying the site) will interfere with the interaction between presynaptic calcium channels and presynaptic vesicles docked to syntaxin or SNAP-25. With the methods and compositions of the present invention, candidate compounds may be screened for those that interrupt the interaction between presynaptic calcium channels and synaptic vesicles by interaction with the herein disclosed target site, which is on the calcium channel but is not involved in calcium influx itself. Thus, the present invention permits the identification of compounds with the desirable properties that, although calcium would still enter through the channel, transmitter release would not occur because the synaptic vesicle would not be properly docked to respond to the locally-increased calcium concentration.

As shown by the disclosure provided herein, N-type presynaptic calcium channels possess amino acid sequences that interact specifically with syntaxin, a presynaptic plasma membrane protein. In particular, syntaxin is shown to directly interact with two adjacent interacting regions within the cytoplasmic loop ($L_{II-III}$) between homologous repeats (domains) II and III of N-type calcium channels. Loop $L_{II-III}$ is a sequence of about 428 amino acids composed from about residues 718 to about 1145 (FIG. 11A) (SEQ ID NO: 2) of the α1 subunit of N-type calcium channels. While the entire $L_{II-III}$ sequence may be used, it is not required as portions of the sequence will suffice. For example, an amino-terminal sequence of about 320 amino acids from about residues 718 to 1037 in FIG. 11A (SEQ ID NO: 2) (or from about residues 717 to 1036 in FIG. 11B) (SEQ ID NO: 3) interact with syntaxin. Other examples of sequences that interact with syntaxin include an amino-terminal sequence of about 142 amino acids from about residues 718 to 859 in FIG. 11A (SEQ ID NO: 2), or an amino-terminal sequence of about 246 amino acids from about residues 718 to 963 in FIG. 11A (SEQ ID NO: 2) (or from about residues 717 to 962 in FIG. 11B) (SEQ ID NO: 3). Further, portions of such amino-terminal sequences may be used for interaction with syntaxin. For example, a sequence of about 87 amino acids (from about residues 773 to 859) interacts specifically with syntaxin.

Similarly, while the entire syntaxin protein may be used, it is not required as portions of the sequence will suffice. For example, a carboxyl-terminal sequence of about 108 amino acids (from about residues 181 to 288 in FIG. 12) interacts with $L_{II-III}$ or portions thereof. It will be evident to those of ordinary skill in the art that based on the disclosure provided herein that smaller segments of syntaxin may be identified that retain the characteristic high affinity interaction described herein between syntaxin and N-type calcium channels.

The disclosure of the present invention also shows that the corresponding two adjacent interacting regions within loop $L_{II-III}$ of the α1 subunit of the P/Q-type calcium channels similarly interact directly with syntaxin. In addition, for example, a portion of the $L_{II-III}$ sequence of the P/Q-type from about residue 722 to 1036 (e.g., FIG. 15) interacts specifically with syntaxin. Again, the $L_{II-III}$ sequence of the P/Q-type binds to the carboxyl-terminal one-third of syntaxin. The P/Q-type and N-type channels compete for the same binding region on syntaxin.

As also shown by the disclosure provided herein, N-type and P/Q-type calcium channels possess amino acid sequences that interact specifically with another presynaptic plasma membrane protein, SNAP-25 (the synaptosome-associated protein of 25 kD). The same two adjacent regions on the N-type and P/Q-type channels that bind syntaxin are also able to bind to SNAP-25. The affinity for binding SNAP-25 is comparable to the affinity for binding syntaxin. The α subunit of N-type ($α_{1B}$) and P/Q-type ($α_{1A}$) channels compete for binding to SNAP-25. Therefore, $α_{1A}$ and $α_{1B}$ interact with identical or overlapping regions on SNAP-25 as well as on syntaxin.

Based on the foregoing, the present invention discloses peptides useful for targeting compounds to disrupt the interaction (e.g., to prevent neurotransmitter release triggered by presynaptic calcium channels) between syntaxin and N-type or P/Q-type calcium channels, or between SNAP-25 and N-type or P/Q-type calcium channels. Peptides may be produced in a variety of ways well known to those in the art. For example, peptides may be derived from native proteins, prepared by synthetic chemistry methodology (including automated peptide synthesis, e.g., using an instrument available from Applied Biosystems, Inc., Foster City, CA), or produced by recombinant DNA techniques (including as fusion proteins expressed in microorganisms such as bacteria). Preferred peptides include those which correspond to the amino acid sequences in FIG. 11A (SEQ ID NO: 2) from amino acid 718 to 1141, from 718 to 1037, from 718 to 963, from 718 to 859, and from 773 to 859.

Based upon the present disclosure, it will be evident to those in the art that useful peptides may be created which contain a sequence identical, or similar, to that of the amino acids in FIG. 11A (SEQ ID NO: 2). For example, the amino terminus of such a peptide may begin at any of the amino acids positioned between (as used herein "between" includes the recited amino acids) amino acid 718 to 773 and the carboxyl terminus may end at any of the amino acids positioned between amino acid 859 to 1141. Alternatively, for example, a peptide may be similar in length to the peptides of amino acids from 718 to 1141 or 718 to 963 (i.e., have a length of about 246 to 424 amino acid residues) and contain an amino acid sequence having at least 60% sequence similarity with the amino acid sequence of FIG. 11A (SEQ ID NO: 2) from amino acids 718 to 963. Particularly preferred peptides include those with about 65%, 70%, 75%, 80%, 85% or greater sequence similarity, and those with about 75%, 80%, 85% or greater sequence identity. Sequence similarity is based upon sequence identity plus conservative substitutions of amino acids. Conservative substitutions include interchanges of valine and isoleucine, leucine and isoleucine, aspartic acid and glutamic acid, and others of a similar nature. When such a peptide has more than 246 residues, the additional amino acids may have, but need not have, sequence similarity to the $L_{II-III}$ sequence. It will be evident to those in the art, when in possession of the present disclosure, that modifications (e.g., additions, deletions and substitutions) may be made to a particular peptide without substantially affecting the peptide's ability to act as a binding partner for SNAP-25, syntaxin, or a binding portion of either.

Additional preferred peptides include the human amino acid sequences known in FIG. 11B (SEQ ID NO: 3) that correspond to the sequences described above from FIG. 11A (SEQ ID NO: 2). For example, preferred peptides include those which correspond to the amino acid sequences in FIG. 11B from amino acid 717 to 1143, from 717 to 1036, 717 to 962, from 717 to 858, and from 772 to 858. The above discussion regarding variations on the preferred peptides from FIG. 11A (SEQ ID NO: 2) is similarly applicable to the preferred peptides from FIG. 11B (SEQ ID NO: 2) and is incorporated here by reference thereto. Other peptides with one or more additions, deletions or substitutions to the sequences described herein may be tested for syntaxin binding and compared to the results disclosed herein for certain preferred peptides. Based upon the results of tests of any other peptides, it will be readily apparent whether a particular peptide is suitable.

Similar to that described above for the calcium channel, an entire syntaxin or SNAP-25 protein may be used, but it is not required as portions of the sequence will suffice. For example, the present invention discloses peptides that are less than an entire syntaxin amino acid sequence, yet still interact specifically with N-type or P/Q-type calcium channels or portions thereof An example of such a peptide is the sequence from amino acids 181 to 288 in FIG. 12. Peptides derived from or based upon native syntaxin or native SNAP-25 and variations (non-naturally occurring) of either are herein collectively termed "syntaxin-like peptides" and "SNAP-25-like peptides," respectively. Such peptides have the ability to interact specifically with N-type or P/Q-type calcium channels or binding portions of either. It will be evident to those in the art, when in possession of the present disclosure, that such peptides may be identified using appropriate assays, such as those described herein.

Presynaptic calcium channel peptides (native) and variations (non-naturally occurring) that possess the ability to bind syntaxin, SNAP-25, or a binding portion of either, are herein collectively termed "calcium channel-like peptides." It will be evident to those in the art, when in possession of the present disclosure, that such peptides may be identified using appropriate assays, such as those described herein. Calcium channel-like peptides may be used to screen for one or more compounds that inhibit the interaction between presynaptic calcium channels and presynaptic vesicles, as mediated by syntaxin or SNAP-25. Assays for screening for such compounds may take a variety of formats, including direct and indirect (e.g., competition or inhibition). In one embodiment, a candidate compound is tested for the ability to bind to a calcium channel-like peptide. For example, a candidate compound may be contacted with such a peptide that contains a reporter group. The reaction conditions (e.g., from about 1 min to 24 hr, at about 4° C. to about 37° C., and a pH of about 6 to 8.5) are sufficient to permit binding between the candidate compound and the peptide if binding is going to occur. The presence of binding is based upon the detection of the reporter group in association with the candidate compound.

In another embodiment, a candidate compound is tested for the ability to inhibit the binding of a calcium channel-like peptide to a syntaxin-like peptide or a SNAP-25-like peptide (i.e., a peptide selected from syntaxin peptides and variations therefrom, or SNAP-25 peptides and variations therefrom, that bind presynaptic calcium channel or calcium channel-like peptide). Any of these peptides may contain a reporter group to detect the binding between the peptides. Alternatively, for example, each peptide may contain a reporter group component that interact upon binding of the peptides. A candidate compound may be incubated simultaneously with both peptides. Alternatively, for example, a candidate compound is incubated with a calcium channel-like peptide to permit binding, if any, between the compound and the peptide. A syntaxin-like peptide or a SNAP-25-like peptide is then contacted with the reaction mixture to permit binding between the calcium channel-like peptide and the syntaxin-like or SNAP-25-like peptide. It may be desirable to include calcium ion in the reaction mixture, e.g., to optimize binding between the peptides. For example, calcium may be included at a concentration of about 10–25 $\mu$M. Where a candidate compound does not bind to the calcium channel-like peptide, the peptide will bind to the syntaxin-like or SNAP-25-like peptide to the same extent as where the compound is absent (e.g., compound replaced in the first step with buffered solution). Thus, the presence of binding between the calcium channel-like peptide and the syntaxin-like or SNAP-25-like peptide is indicative that the candidate compound did not bind to the former peptide. However, where a candidate compound does bind to the calcium channel-like peptide, the peptide is no longer available to bind to the syntaxin-like or SNAP-25-like peptide. Thus, the absence of binding between the calcium channel-like peptide and the syntaxin-like or SNAP-25-like peptide is indicative that the candidate compound does bind to the former peptide. All of the above discussion is equally applicable where a syntaxin-like peptide is replaced with syntaxin (i.e., a full length syntaxin protein) or a SNAP-25-like peptide is replaced with SNAP-25 (i.e., a full length SNAP-25 protein).

Detection of binding between a compound and peptide or between two peptides may be accomplished by a variety of known techniques, including radioassays and enzyme linked assays. For detection purposes, a peptide can be directly labeled with a reporter group. Alternatively, a molecule (e.g., an antibody) that binds to a peptide or candidate compound can possess a reporter group. The reporter group can include radioisotopes, fluorophores, enzymes, luminescers, or dye particles. These and other labels are well known in the art and are described, for example, in the following U.S. Pat. Nos. 3,766,162; 3,791,932; 3,817,837; 3,996,345; and 4,233,402.

The methods described herein may be used in a fully or partially automated format for high through-put screening of candidate compounds. For example, peptides may be utilized in a 96-well plate assay format with a reporter group amenable to automated analysis of the results. For example, the reporter group can be chosen from a variety of enzymes, including horseradish peroxidase, beta-galactosidase, alkaline phosphatase and glucose oxidase. The results of the reaction between an enzyme and its added substrate can be read optically in a 96-well plate reader.

Alternative formats, labeling and in general other modifications of the assays described above are within the scope of those in the art.

The methods and compositions of the present invention have a variety of uses. A particularly preferred use of the present invention is to screen for compounds that differentially modulate transmitter release versus current flow via calcium channels. Compounds may be identified that inhibit neurotransmitter release without significantly affecting calcium influx. Although calcium would still enter through presynaptic calcium channels, transmitter release would not occur because the synaptic vesicles would not be properly docked to respond to the locally increased calcium concentration. Such compounds would effectively block release of neurotransmitters in the central or peripheral nervous system and be useful in neuroprotection from excitotoxicity in many clinical settings, including the treatment of stroke, cognitive deficit related to cardiac surgery, and neuronal damage during acute epileptic episodes.

The following examples are offered by way of illustration and not by way of limitation.

EXAMPLES

Example 1

Construction and Expression of Recombinant GST- and His-Fusion Proteins

GST-Syntaxin 1A fusion proteins were generated by cloning amplified portions of the gene corresponding to the full-length (2–289), N-terminal region (2–190) and C-terminal region (181–289) of rat syntaxin 1A (Yoshida et al., *J. Biol. Chem.* 267:24925–24928, 1992; Bennett et al., *Science* 257:255–259, 1992) were amplified by PCR. EcoRI and XhoI sites were included at the ends of the N-terminal and C-terminal oligonucleotide primers, respectively; stop codons were included in both oligonucleotides. The amplified material was then cloned into EcoRI/XhoI digested pGEX-4T expression vector (Pharmacia LKB Biotechnology) to obtain in-frame recombinant proteins fused to glutathione S-transferase (GST).

A GST fusion protein including full-length SNAP-25 was similarly prepared by ligating a EcoRI-XhoI fragment of SNAP-25 (Oyler et al., *J. Cell Biol.* 109:3039–3052, 1989; amplified by PCR with synthetic oligonucleotides including the appropriate restriction sites) into the pGEX4T vector (Pharmacia LKB).

His-fusion proteins of $\alpha_{1B}$ were generated by amplification from oligonucleotides flanking a series of cytoplasmic domains of the α1 subunit of rat class B N-type calcium channels and containing appropriate restriction sites and in-frame stop codons. Polymerase chain reaction was performed using $\alpha_{1B}$ cDNA (rbB-1) as a template (Dubel et al., *Proc. Natl. Acad. Sci. USA* 89:5058–5062, 1992) to amplify the appropriate DNA fragments. The amplified products were directionally cloned into the pTrcHis C expression vector (Invitrogen) that codes for a stretch of 6 histidine residues immediately following the initiator codon. The His-fusion proteins containing various cytoplasmic domains/loops of calcium channel $\alpha1_B$ were as follows: the cytoplasmic amino-terminal, His-NT (41–94); the loops between domains I and II, His-$L^{I\text{-}II}$ (357–483); the loops between domains II and III, His-$L_{II\text{-}III}$ (718–1145); the loops between domains III and IV, His-$L_{III\text{-}IV}$ (1418–1474); the cytoplasmic carboxyl-terminal 1, His-CT-1 (1712–2068) and II, His-CT-2 (2044–2336); fragments between domains II and III, His-$L_{II\text{-}III}$ (718–859), His-$L_{II\text{-}III}$ (832–963), His-$L_{II\text{-}III}$ (940–1051), His-$L_{II\text{-}III}$ (1027–1145), His-$L_{II\text{-}III}$ (718–825), His-$L_{II\text{-}III}$ (744–859), His-$L_{II\text{-}III}$ (773–859); the cytoplasmic loops between domains II and III of $\alpha1_A$ (723–868) and $\alpha1_S$ (670–800). All constructs were verified by determining the DNA sequence.

Constructs were transformed into a protease-deficient strain, BL26 (Novagen). Fusion protein expression was obtained following the basic protocol of Smith and Johnson (*Gene* 67:31–40, 1988). In brief, fresh overnight cultures were diluted 1:10 in YT medium containing 100 μg/ml ampicillin and 2% glucose and incubated for 4 hr at 37° C. with shaking. After 2 hr of growth, isopropyl-β-D-thiogalactopyranoside (IPTG) was added to a final concentration of 0.5 mM. Bacterial cells were pelleted by centrifugation at 5000×g for 10 min at 4° C. and resuspended in PBS buffer. The bacteria were lysed by mild sonication and solubilized by the addition of Triton X-100 to final concentration of 1% followed by incubation for 30 min on ice.

A hBI clone was isolated by screening a cDNA library generated from the human small cell lung carcinoma line, SCC-9 (Oguro-Okano et al., *Mayo Clinic Proceedings* 67:1150–1159, 1992). Briefly, ~500,000 cDNAs were screened with a randomly primed $^{32}$P-radiolabelled 1.9 kb Eco RI fragment from the rat brain class A cDNA, rbA-73 (Snutch et al., *Proc. Natl. Acad. USA* 87:3391–3395, 1990). Hybridization was carried out overnight at 62° C. in 5X SSPE (1X SSPE=0.18 M NaCl, 1 mM EDTA, 10 mM sodium phosphate, pH 7.4), 0.3% SDS, 0.2 mg/ml denatured salmon sperm DNA. Filters were washed 4 times for 20 min in 0.5X SSPE at 60° C. A human brain BI clone was isolated by screening a human hippocampus cDNA library (Stratagene, La Jolla, Calif.) with a $^{32}$P-radiolabelled 1.3 kb Eco RV-Sst I fragment of the small cell lung carcinoma cDNA. DNA sequencing was performed on double-strand plasmid DNA with modified T7 polymerase (Sequenase 2.0, USB Corp., Cleveland, Ohio).

His-fusion proteins of aIA were generated using cDNAs encoding the rat brain rbA-126 isoform (Starr et al., *Proc. Natl. Acad. Sci. USA* 88:5621–5625, 1991) and a human homolog of the BI-1 isoform (see above) from a small cell lung carcinoma cell line (Oguro-Okano et al, *Mayo Clinic Proceedings* 67:1150–1159, 1992) as a template and synthetic oligonucleotides with overhanging restriction sites as primers in a polymerase chain reaction. The amplified products were directionally cloned into the pTrcHis expression vector (Invitrogen) to yield cDNAs expressing the His-fusion proteins rbA 724–869, rbA 844–981, rbA 724–981, hBI 722–895, hBI 843–1036, and hBI 722–1036. Constructions of full-length GST-syntaxin 1A, GST-syntaxin 1A N-terminus, GST-syntaxin 1A C-terminus and His-fusion proteins of the N-type $Ca^{++}$ channel were performed as described above. All constructs were verified by DNA sequence analysis. The protease-deficient Escherichia coli strain BL26 (Novagen) was used for expression following standard protocols (Smith and Johnson, *Gene* 67:31–40, 1988). Briefly, fresh overnight cultures were diluted 1:10 in LB medium containing ampicillin (100 μg/ml), incubated for 90 min at 37° C. with shaking and induced upon addition of 0.5 mM isopropyl-β-D-thiogalactopyranoside (IPTG). After 2–4 h growth, bacterial cultures were pelleted by centrifugation at 5000×g for 10 min at 4° C. and resuspended in PBS buffer (140 mM NaCl, 2.7 mM KCl, 10.1 mM $Na_2HPO_4$, 1.8 mM $KH_2PO_4$ pH 7.3) containing protease inhibitors (pepstatin, aprotinin, leupeptin (each at 4 μg/ml), 0.4 μM phenylmethylsulfonyl fluoride). The bacteria were then lysed by mild sonication, solubilized by adding Triton X-100 to a final concentration of 1% and incubated for 30 min on ice. The suspension was centrifuged at 15,000 rpm for 15 min and the supernatant stored in aliquots at −20° C. The amount of each fusion protein in the supernatant was estimated with a standard curve relating the intensity of the immunoblotting signal to the amount of a standard fusion protein (T7 gene 10, Novagen) applied. The pixel values for the $Ca^{++}$ channel fusion proteins used were as follows: rbB 718–859, 1288; rbB 832–963, 1077; rbB 718–963, 405; rbA 724–869, 856; rbA 844–981, 274; rbA 724–981, 1117; BI 722–895, 1258; BI 843–1036,321; BI 722–1036, 1154.

Example 2

Screening of His-Fusion Proteins for Binding to GST-Syntaxin

Binding of the cytoplasmic domains/loops of calcium channels to GST-syntaxin fusion proteins was assayed. Approximately 2 μg of GST-syntaxin fusion proteins or GST alone was bound to glutathione-Sepharose 4B beads (Pharmacia) in PBS (140 mM NaCl, 2.7 mM KCl, 10.1 mM $Na_2HPO_4$, 1.8 mM $KH_2PO_4$, pH 7.3) containing 0.5% Triton X-100, 4 μg/ml pepstatin, 4 μg/ml aprotinin, 4 μg/ml leupeptin and 0.4 μM phenylmethylsulfonyl fluoride. The mixture was incubated at 4° C. for 1 hour with constant agitation. Following incubation, the beads were washed with PBS to remove uncoupled GST fusion proteins. Glutathione-Sepharose beads preincubated with similar amounts of GST-syntaxin or GST were added to the lysates containing 5–10 μg His-fusion proteins of the various cytoplasmic domains/loops of calcium channels and incubated with gentle mixing for 3 hr at 4° C. Following incubation, beads were washed three times in ice-cold PBS with 0.1% Triton X-100, three times in 50 mM Tris-HCl, pH 8.0/140 mM NaCl/0, 1% Triton X-100, and once in 50 mM Tris-HCl, pH 8.0.

Bound fusion proteins were eluted with 50 mM Tris-HCl, pH 8.0/15 mM glutathione for 20 min with gentle mixing and eluates were separated from the beads by centrifugation at 10,000×g for 1 minute. Fusion proteins were electrophoresed on SDS/PAGE and transferred to nitrocellulose. Specific fusion proteins were detected by an ECL kit (Amersham) using either an anti-GST or T7-Tag antibody (Novagen). The T7-Tag antibody is a mouse monoclonal directed against the 12 amino acid leader peptide in the N-terminal of His-fusion proteins. To assess the quantity and quality of the His-fusion proteins used in binding assays, approximately 10% amount of lysates was examined by SDS/PAGE and immunoblotting. The amount of each fusion protein in the binding assays was estimated with a standard curve relating the intensity of the immunoblotting signal to the amount of a standard fission protein.

Figure 2:
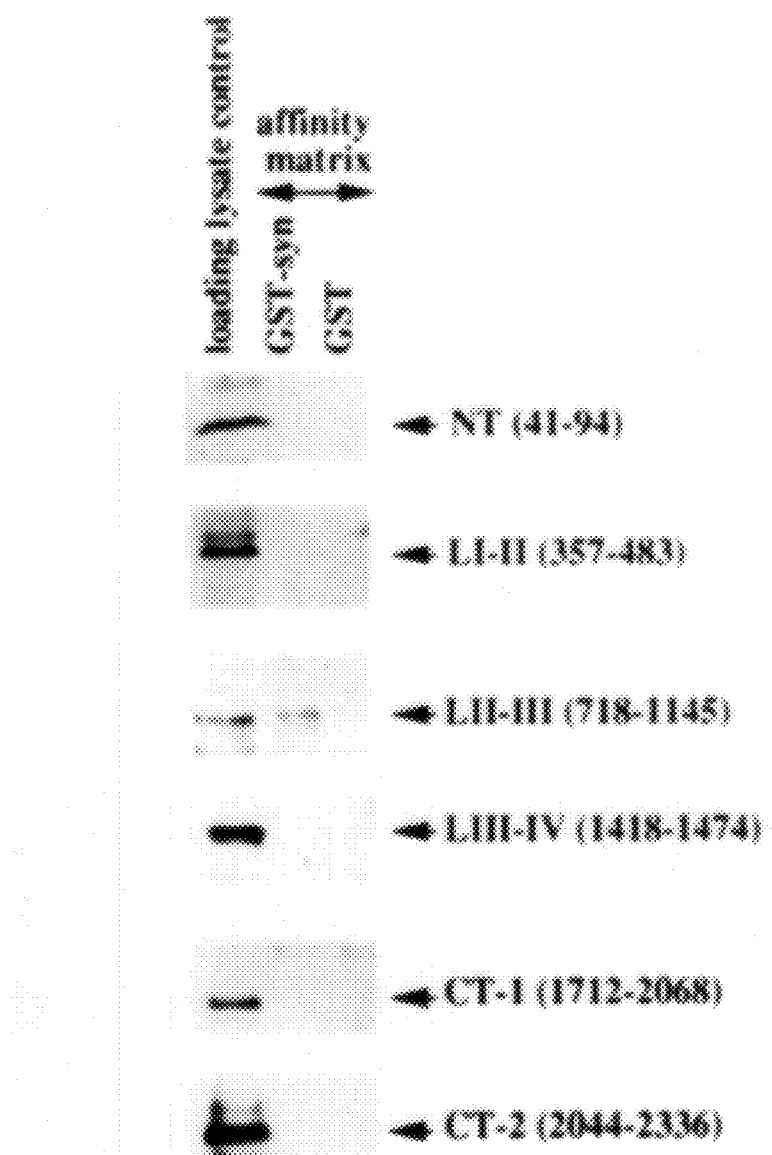
FIG. 2 is immunoblots (Panels A and B) that demonstrate the interaction of the cytoplasmic loop $L_{II-III}$ (718–1145) of α1B with syntaxin 1A. Approximately 2 μg of GST-syntaxin (GST-syn) or GST coupled to glutathione-Sepharose 4B beads were incubated with 5–10 μg of the indicated various His-fusion proteins. Specifically-bound proteins were eluted by 15 mM glutathione/50 mM Tris-HCl, pH 8, separated by SDS/PAGE, electrophoretically transferred to nitrocellulose, and probed for the presence of His-fusion proteins by immunoblotting with anti-T7-Tag antibody. Left lane, aliquots of lysates containing His-fusion proteins as indicated; center lane, eluate from GST-syntaxin affinity matrix; right lane, eluate from GST affinity matrix.

Interaction of His-$L_{II-III}$ (718–1145) with GST-syntaxin fusion protein was observed as a specific band as illustrated in FIG. 2 (middle lane, GST-syn). In contrast, no interaction was detected with GST alone (FIG. 2, right lane). All other His-fusion proteins containing the cytoplasmic loops, as well as the N- and C-terminal of $\alpha 1_B$ failed to demonstrate specific interaction with GST-syntaxin (FIG. 2), even though comparable quantities of the expressed proteins were analyzed. These results suggest that there is a specific interaction between the cytoplasmic loop connecting domains II and III of $\alpha 1_B$ and syntaxin 1A.

Figure 3:
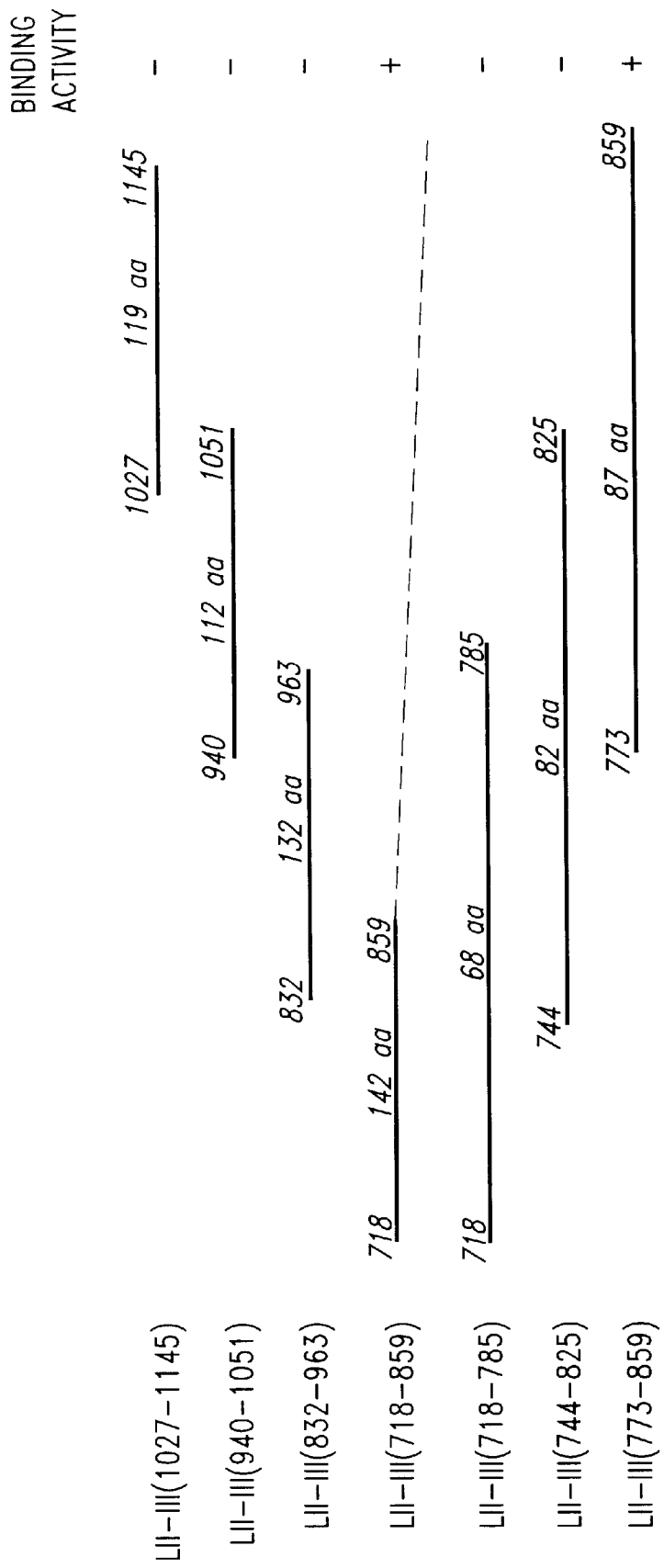
FIG. 3 is a schematic representation of the His-fusion proteins containing various sequences from the cytoplasmic loop $L_{II-III}$ (718–1145).
Figure 4A:
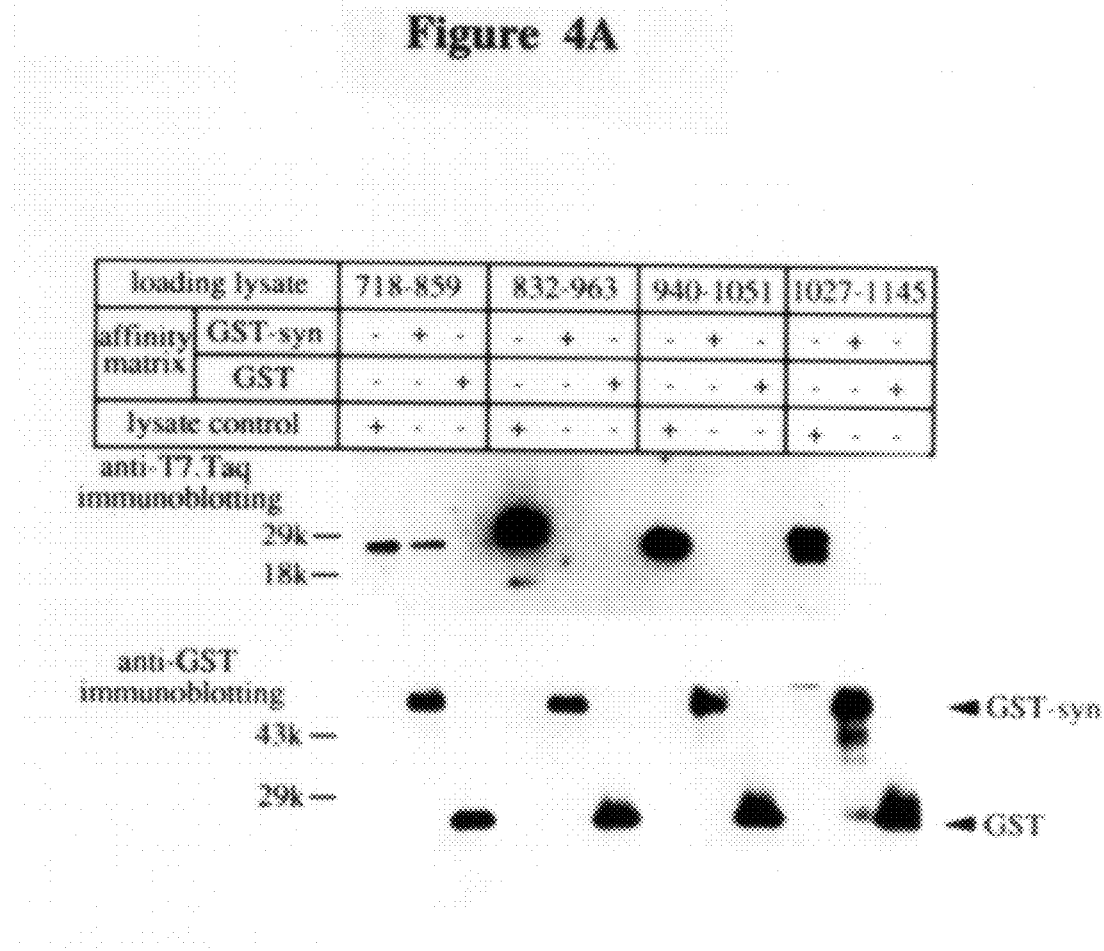
FIGS. 4A and 4B are immunoblot analyses of the interaction of fusion proteins containing sequences from loop $L_{II-III}$ (718–1145) with syntaxin 1A. The indicated His-fusion proteins were incubated with GST-syntaxin (GST-syn) and GST affinity matrices. Bound proteins were eluted and detected on immunoblots with anti-T7-Tag antibody. To normalize for the amounts of GST-syn or GST fusion proteins bound to affinity matrix and eluted, the blots were stripped and probed with anti-GST antibody.
Figure 4B:
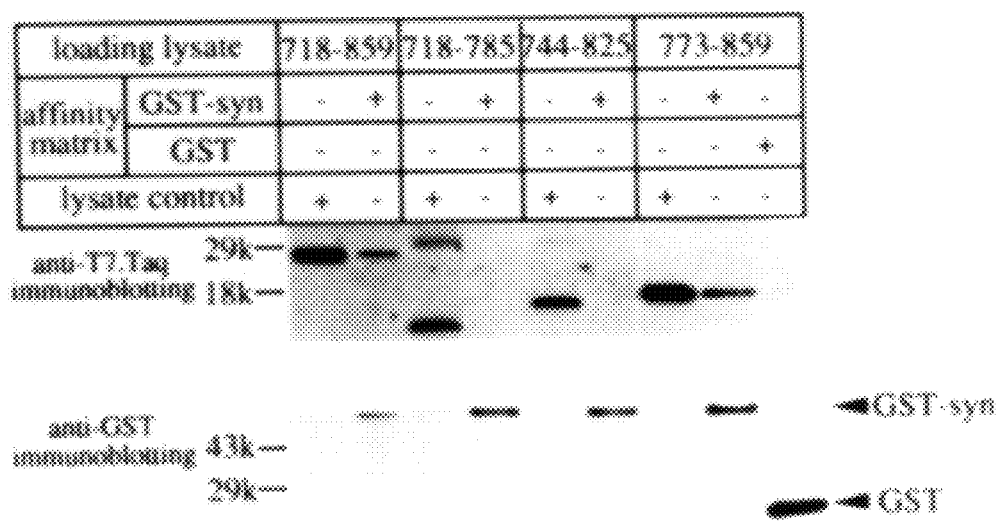
Figure 5:
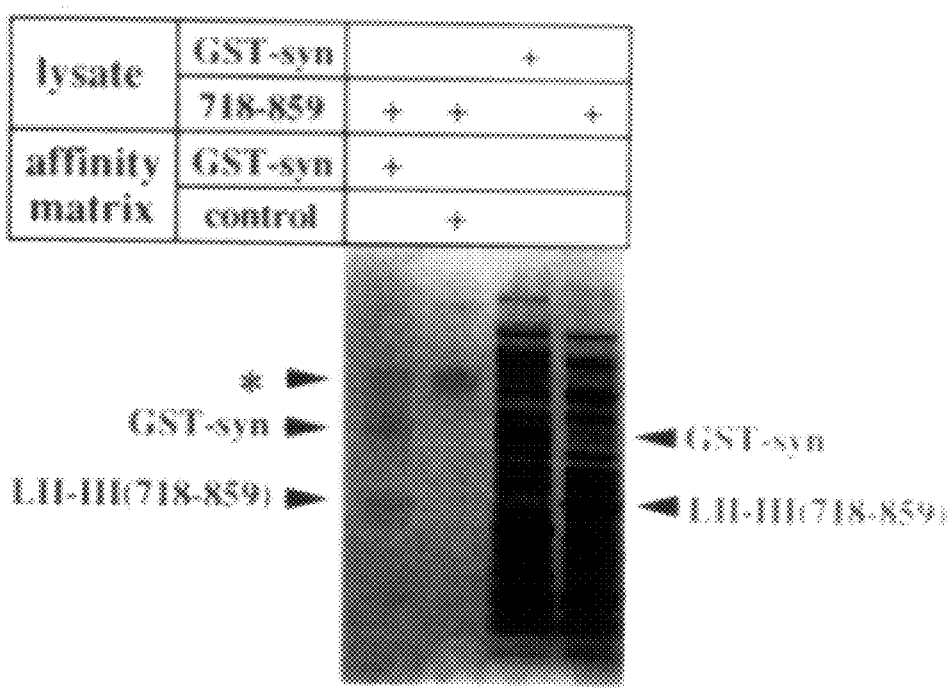
FIG. 5 is a Coomassie blue-stained polyacrylamide gel showing the specificity of the binding of GST-syntaxin to $L_{II-III}$(718–859). Total bacterial lysate containing His-$L_{II-III}$ (718–859) fusion protein was incubated with glutathione-Sepharose-4B beads prebound by bacterial lysate containing GST-syntaxin fusion protein (GST-syn) or bacterial lysate without any fusion protein (control) as indicated. Complexes of GST-syntaxin and $L_{II-III}$(718–859) were eluted and analyzed by SDS-PAGE and Coomassie blue staining. Migration positions of GST-syn, $L_{II-III}$(718–859), and a non-specific glutathione-Sepharose binding bacterial protein of ~70 kDa (*) are indicated.
Figure 6:
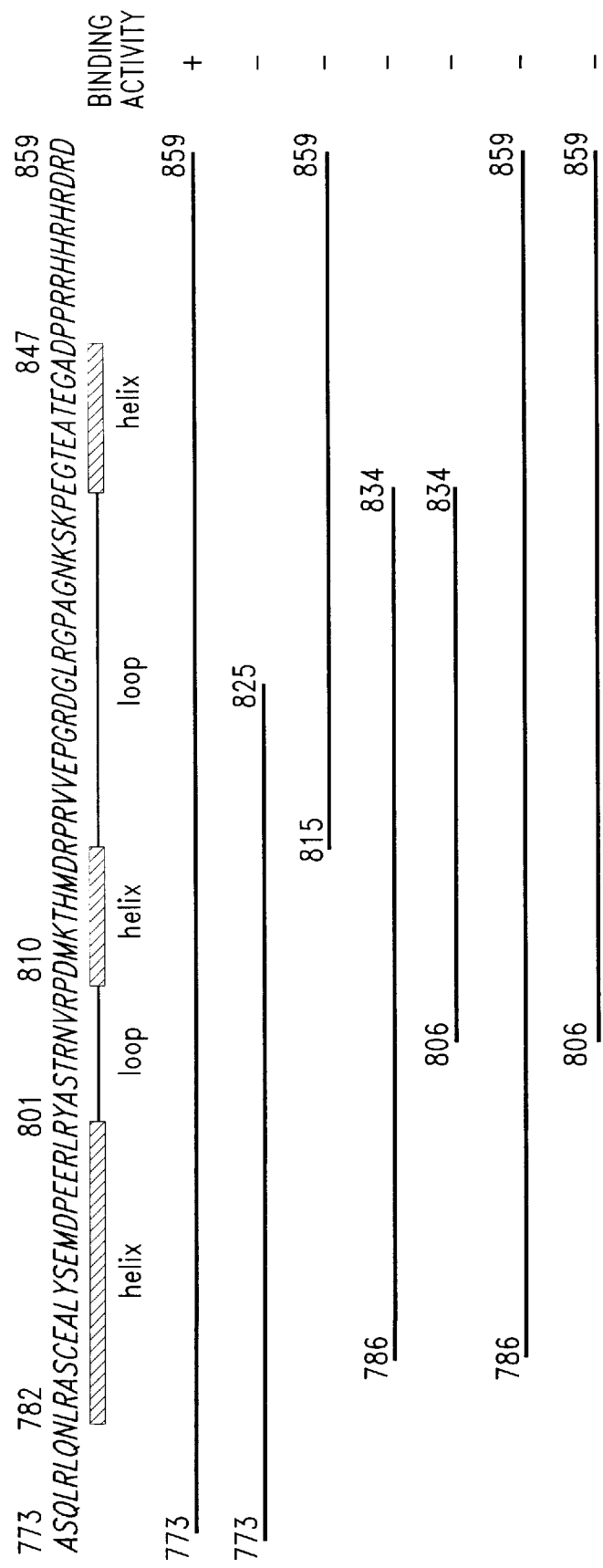
FIG. 6 shows a sequence analysis of the syntaxin-binding site and location of two overlapping helix-loop-helix motifs within the $L_{II-III}$(773–859) region (SEQ ID NO: 1). Underneath the locations of amino acids used to generate six new His-fusion proteins are shown. The binding activity of each deleted fusion protein is listed in the right column.
Figure 7:
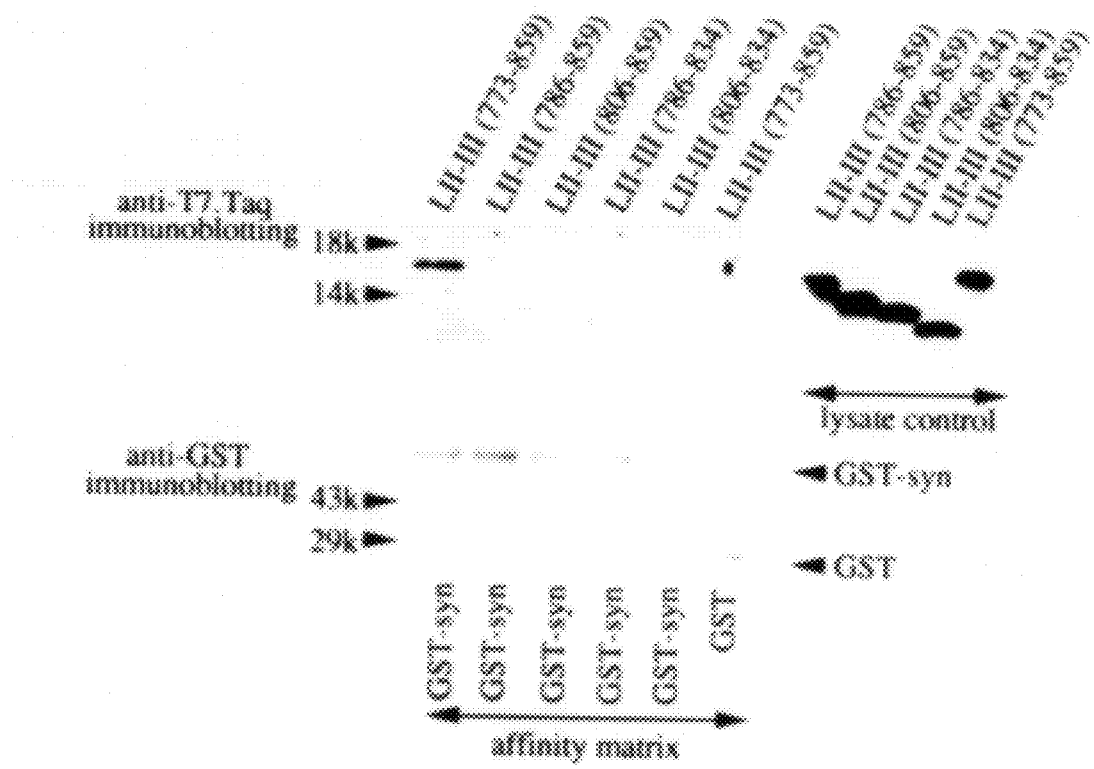
FIG. 7 is an immunoblot demonstrating that deletion mutants of the helix-loop-helix structure completely abolished syntaxin-binding activity. Approximately 5 μg of His-fusion proteins from four of the six deletion mutants shown in FIG. 6 and the complete 87-residue peptide (773–859) (SEQ ID NO: 1) were incubated with affinity matrix containing 2 μg of GST-syn or GST. The bound His-fusion proteins were eluted and probed with anti-T7-Tag antibody (top). Controls for quantity and quality of His-fusion proteins are shown in the top right panel. The amounts of GST-syntaxin (GST-syn) or GST fusion proteins attached and eluted from matrix were determined by a second blotting with anti-GST antibody shown in bottom panel.

In order to investigate the minimum sequence requirements for binding to syntaxin 1A, a series of His-fusion proteins covering various lengths of $L_{II-III}$ were generated and analyzed for binding (FIG. 3). As shown in FIG. 4, the amino-terminal 142 amino acids (718–859) from $L_{II-III}$ are sufficient for binding to syntaxin 1A. Larger quantities of fusion proteins containing the remaining 286 amino acids (residues 860–1145) located in $L_{II-III}$ do not interact detectably with syntaxin 1A.

Further analysis of fusion proteins containing overlapping portions of the segment from residue 718 to 859 (FIG. 3) indicated that a sequence of 87 amino acids (773–859) of $\alpha 1_B$ was sufficient for interaction with syntaxin 1A (FIG. 4, right column). In contrast, the fusion peptides $L_{II-III}$ (718–785) and $L_{II-III}$ (744–825) do not interact specifically with syntaxin since no interaction was observed when they were incubated with the GST-syntaxin matrix (FIG. 4, middle columns). Thus, the first 56 residues (718–773) of $L_{II-III}$ are unlikely to be required for the syntaxin-binding site since His-$L_{II-III}$ (718–785) did not show any binding activity while His-$L_{II-III}$ (773–859) retained the full binding of the longer fusion peptide His-$L_{II-III}$ (718–859).

Figure 8:
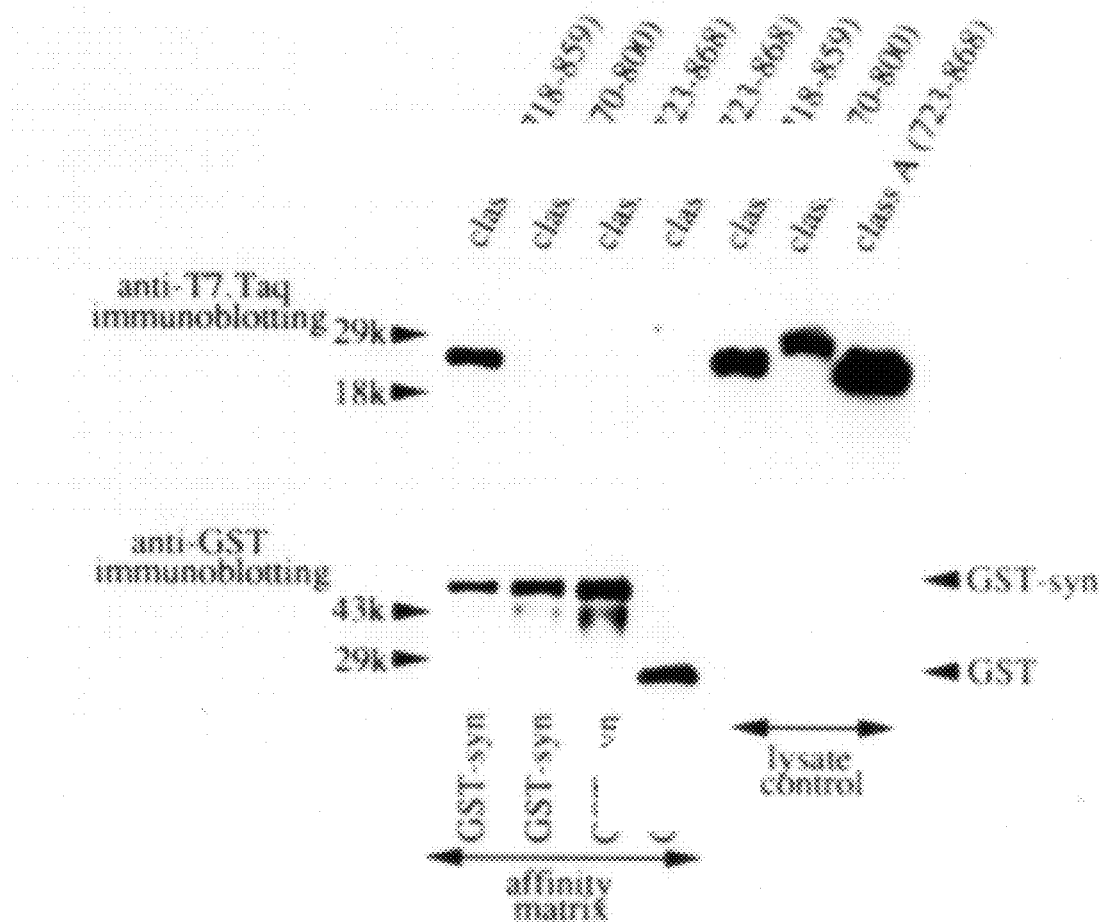
FIG. 8 is an immunoblot showing the interaction of the corresponding regions from $\alpha1_A$ and $\alpha1_S$ with syntaxin 1A. His-fusion proteins with the corresponding region (723–868) of the cytoplasmic loop $L_{II-III}$ of class A calcium channel and the entire $L_{II-III}$ loop (670–800) of L-type rabbit skeletal muscle calcium channel (class S) were expressed. The binding assays were performed as described for FIG. 2. Aliquots of lysates as indicated were incubated with GST-syntaxin (GST-syn) or GST-glutathione-Sepharose beads. Bound proteins were eluted and resolved by electrophoresis in SDS/PAGE and sequentially probed with anti-T7-Tag (top panel) and anti-GST (bottom panel) antibodies.
Figure 9:
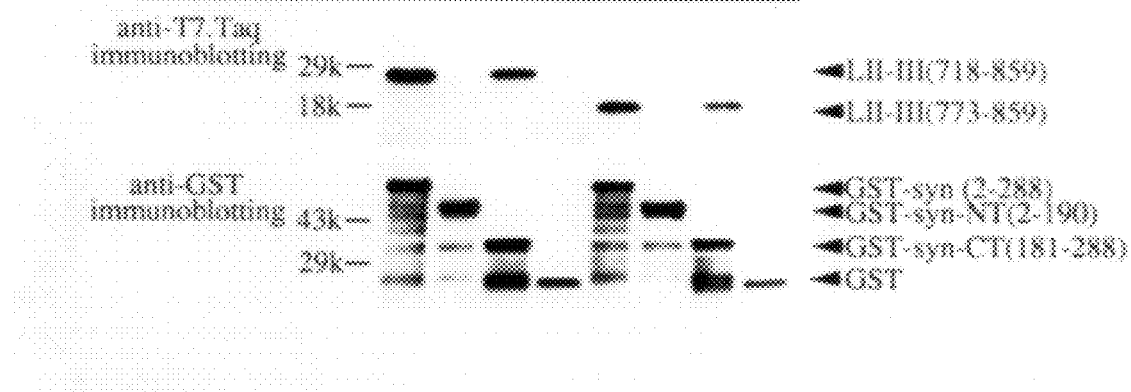
FIG. 9 is an immunoblot demonstrating the interaction of the amino and carboxyl terminal domains of syntaxin 1A with N-type calcium channels. Two GST-syntaxin fusion proteins containing the amino-terminal sequence, GST-syn-NT(2–190), and the carboxyl-terminal sequence, GST-syn- CT(181–288), were generated and used for affinity matrices. Approximately 2 μg of both His-fusion proteins, $L_{II-III}$ (718–859) and $L_{II-III}$(773–859), containing the syntaxin-binding site, were loaded on affinity matrices with GST-syn, GST-syn-NT, GST-syn-CT, and GST. As indicated, bound His-fusion proteins were co-eluted with GST-fusion proteins and immunoblotted sequentially with anti-T7-Tag (top panel) and anti-GST (bottom panel) antibodies.

To test whether $\alpha 1_A$ shares a similar syntaxin binding activity to $\alpha 1_B$, His-fusion proteins containing the corresponding region (residues 723–868) of the cytoplasmic loop $L_{II-III}$ from $\alpha 1_A$ (Starr et al., Proc. Natl. Acad. Sci. USA 88:5621–5625, 1991) were constructed. As a control, a His-fusion protein covering the entire $L_{II-III}$ loop (residues 670–800) of the rabbit skeletal muscle L-type calcium channel ($\alpha 1_S$) (Tanabe et al., Nature 328:313–318, 1987) was included in parallel syntaxin-binding assays. As shown in FIG. 8, while the sequence (718–859) from $\alpha 1_B$ binds to GST-syntaxin, there is no detectable interaction between the corresponding region from $\alpha 1_A$ or $\alpha 1_S$ in the syntaxin-binding region. These results indicate that these weakly conserved regions of the cytoplasmic loop $L_{II-III}$ from class A and class S calcium channels do not bind to syntaxin.

Example 3

Partial Purification of Rat Class B N-Type Calcium Channels

Brain calcium channels were partially purified as previously described (Westenbroek et al., Neuron 9:1099–1115, 1992). Briefly, fifteen rat brains cortices from three-week-old Sprague-Dawley rats were homogenized in 130 ml of 320 mM sucrose, 5 mM Tris pH 7.4 and protease inhibitors (1 µg/ml each pepstain A, leupeptin, and aprotinin, 0.2 mM phenyl methanesulfonyl fluoride, and 0.1 mg/ml benzamidine) by 10 strikes with a glass-Teflon homogenizer. After a short centrifugation (5000 rpm, 2 minutes, SS34-rotor), the membranes contained in the supernatant were pelleted (42,000 rpm, 1 hour, in Ti45 rotor) and solubilized in 230 ml of 1.2% digitonin in PBS (150 mM NaCl, 300 mM KCl, and 10 mM sodium phosphate buffer (pH 7.4) for 15 min on ice. Unsolubilized material was sedimented by centrifugation as before, and the supernatant was slowly poured over a 20 ml wheat germ agglutinin (WGA) Sepharose column (50 ml/hr.). The column was washed with 300 ml of 0.1% digitonin, 75 mM NaCl, 50 mM sodium phosphate, 10 mM Tris-HCl (pH 7.4) at a flow rate of 50 ml/hr.

Bound calcium channels were eluted with 100 mM N-acetyl-D-glucosamine in the same buffer at a flow rate of 50 ml/hr. Two ml fractions were collected, frozen and stored at −80° C. About 50% of the solubilized N-type calcium channels were specifically bound and eluted from WGA-Sepharose under these experimental conditions (Westenbroek et al., Neuron 9:1099–1115, 1992).

Example 4

Immunoprecipitation

The WGA extraction fraction was labeled for 2 hr on ice with 500 fmol [$^{125}$I]Tyr$^{22}$-ω-CTx-GVIA (NEN-Dupont), diluted 10-fold with PBS, and incubated for 2 hr at 4° C. with either anti-CNB-1 antibody, which is directed against residues 851–867 of the β1 subunit of rat brain class B N-type calcium channel (Westenbroek et al., Neuron 9:1099–1115, 1992) or mAb 1OH5, an anti-syntaxin antibody (Yoshida et al., J. Biol. Chem. 267:24925–24928, 1992). Immune complexes were recovered by the addition of 4 mg of protein A-Sepharose 4B swollen in TBS, rotation for 1 hour, and centrifugation. After three washes in PBS, immunoprecipitated radioactivity was counted.

Anti-CNB1 antibodies immunoprecipitated 85%±6% (n=3) of ω-CTx receptors were also immunoprecipitated by anti-syntaxin antibody mAb10H5, but not by control mouse IgG (1.6%±0.4%, n=3), indicating that only a small fraction of N-type channels remains associated with syntaxin after treatment with digitonin and subsequent WGA-Sepharose column purification. Thus, this procedure provides N-type calcium channels containing $\alpha 1_B$ with only 12% of their syntaxin-binding sites occupied.

Example 5

Inhibition of Binding of [125I]-ω-CTx-GVIA-Labeled N-Type Calcium Channels by the His-$L_{II-III}$ (773–859) Peptide Approximately 2 µg of either GST-syntaxin or GST were coupled to glutathione-Sepharose 4B beads in PBS/0.5%

Triton X-100 for 1 hour at 4° C. After removal of unbound proteins by washing with PBS/0.1% Triton X-100 for three times, an equal amount of lysate containing either His-$L_{II-III}$ (773–859) or His-$L_{II-III}$ (1027–1145), as a non-inhibitor control, was added to the beads. After a 1 hr incubation, an equal amount of cpm of [125I]-ω-CTx-GVIA-labeled N-type calcium channel was added to each reaction mixture. After a further 3 hour incubation, the beads were washed three times with PBS and the amount of bound receptor was assessed by direct counting.

As shown in FIG. 10B, GST-syntaxin bound 3276±191 cpm (n=3) of labeled N-type channels, whereas GST alone bound only 549±74 cpm (n=3). This observation shows directly that syntaxin can bind N-type calcium channels in vitro and strengthens the conclusion that N-type calcium channels are tightly associated with syntaxin (Bennett et al., *Science* 257:255–259, 1992; Lévêque et al., *J. Biol. Chem.* 269:6306–6312, 1994; Yoshida et al., *J. Biol. Chem.* 267:24925–24928, 1992; O'Conner et al., *FEBS Lett.* 326:255–261, 1993). These results also confirm that GST-syntaxin fusion proteins attached to an affinity matrix maintain the binding activity for calcium channels.

In order to demonstrate that the binding sequence identified in in vitro binding assays represents the high affinity syntaxin-binding site in $\alpha 1_B$, the ability of the 87-amino-acid binding peptide to compete for binding of native N-type calcium channels to GST-syntaxin was analyzed. Peptide competition analysis demonstrated that the peptide, His-$L_{II-III}$ (773–859), specifically competed for the binding of N-type calcium channels to GST-syntaxin (FIG. 10C). In three independent experiments, a 78%±12% reduction in the specific binding of ω-CTx-labeled N-type calcium channels to GST-syntaxin in the presence of lysate containing peptide His-$L_{II-III}$ (773–859) was observed. Only a 10%±8% reduction was seen in the presence of a control lysate containing approximately the same amounts of the peptide His-$L_{II-III}$ (1027–1145), which contains the carboxyl terminus of $L_{II-III}$.

Example 6

Binding Assays and Immunoblot Analysis
A. In Vitro Binding Assays

GST fusion proteins (150 pmol) were bound to glutathione agarose beads (30 μl, Pharmacia LKB) in PBS (140 mM NaCl, 2.7 mM KCl, 10.1 mM $Na_2HPO_4$, 1.8 mM $KH_2PO_4$ pH 7.3) containing 0.1% Triton X-100, pepstatin, aprotinin, leupeptin (each at 4 μg/ml), 0.4 ,M phenylmethylsulfonyl fluoride. The mixture was incubated at 4° C. for 1 hr with constant agitation. The beads were then washed with PBS and incubated with identical concentrations of expressed His-fusion proteins of different $Ca^{++}$ channels for 3 hr at 4° C. Beads were then washed three times in ice-cold PBS/0.1% Triton X-100 and two times in 50 mM Tris-HCl pH 8/0.1% Triton X-100. Bound proteins were eluted from the beads by competition with 15 mM reduced glutathione/ 50 mM Tris-HCl pH 8 (20 μl) for 20 min with gentle mixing. Eluates were separated from the beads by centrifugation at 10,000×g for 1 min, mixed with 10 μl 3× Tricine sample buffer and boiled for 2 min.
B. Immunoblot Analysis Proteins were separated on 10–20% Tricine gradient gels (Novex) and transferred overnight to nitrocellulose (0.45 μm, Schleicher & Schuell). The membrane was then incubated with 5% powdered milk in TBS (10 mM Tris pH 8, 150 mM NaCl, and 0.1% Tween 20) for 1 h at room temperature. Blots were washed three times in TBS and incubated with Anti-T7.Tag monoclonal antibody (1:10,000, Novagen) for 1 h at RT. Following three washes with TBS, incubation with Anti-mouse IgG conjugated with horseradish peroxidase (1:10,000, Amersham) was performed. Blots were then washed for 1 h with TBS and the immunoreactive bands were visualized by enhanced chemoluminescence (ECL system, Amersham). Bound antisera were quantitated by phosphorimaging (Molecular Dynamics). The pixel values for FIG. 14 were rbB 718–859, 45; rbB 832–963, 751; and rbB 718–963, 1646.

Example 7

Identification of a Second Syntaxin-binding Segment in the $\alpha_{1B}$ Subunit of N-type $Ca^{++}$ Channels As shown above, a syntaxin-binding site on the N-type $Ca^{++}$ channel was identified using in vitro binding assays. Deletion analysis revealed a minimum requirement of 87 amino acids in the intracellular loop $L_{II-III}$ (rbB 773–859, FIG. 13) to maintain binding activity. However, the affinity of $Ca^{++}$ channel fusion proteins for syntaxin is progressively reduced as their size is decreased toward the minimum sequence of 87 amino acid residues. Therefore, binding studies with larger fusion proteins of $L_{II-III}$ were performed to identify additional regions which influence the affinity of syntaxin binding. In order to be able to draw conclusions about the binding affinities, equal concentrations of the fusion proteins were used in each binding assay by relating the intensity of the immunoblotting signal of each fusion protein lysate to a standard curve established for a standard fusion protein. As shown in FIG. 14, rbB 718–963 binds with approximately 40-fold higher affinity to syntaxin than rbB 718–859. The contribution of rbB 832–963 can account for this difference in affinity as the sum of signal intensities of rbB 718–859 and rbB 832–963 is approximately equal to the intensity of rbB 718–963. No binding to GST alone was detected for all three fusion proteins (FIG. 14, right lanes), demonstrating the specificity of the interactions. Therefore, the syntaxin-binding site of N-type $Ca^{++}$ channel is composed of two different regions of the intracellular loop $L_{II-III}$.

Example 8

Isoforms of $\alpha_{1A}$

Screening of cDNA libraries generated from human hippocampus and a small cell carcinoma cell line (Oguro-Okano et at., *Mayo Clinic Proceedings* 67:1150–1159, 1992) resulted in the isolation of clones encoding a human homologue of the BI isoform of $\alpha_{1A}$. The predicted amino acid sequences of the human hippocampal and small cell carcinoma BI isoforms were identical in the $L_{II-III}$ region and share 92% and 82% identity with the rabbit BI and rat rbA isoforms, respectively (FIG. 15). Of particular note, alignment of the three sequences shows that relative to rbA, the human $\alpha_{1A}$ isoform contains several insertions of nearly identical sequence at the same positions as those of rabbit BI, indicating that the human $\alpha_{1A}$ cDNAs correspond to the BI isoform. These observations support the hypothesis that BI and rbA are different isoforms of $\alpha_{1A}$ which may be present in all three species.

Based on the binding behavior of the $\alpha_{1B}$ fusion proteins described above, corresponding histidine-tagged (His)-fusion proteins of the $L_{II-III}$ regions of the human BI (hBI) isoform and the rat rbA isoforms were generated. Recombinant GST-syntaxin or GST alone was bound to glutathione-Sepharose beads and incubated with equal concentrations of the six $\alpha_{1A}$ His-fusion proteins. Immunoblot detection revealed that the largest fusion protein of the hBI isoform (hBI 722–1036) is able to bind with high affinity to GST-syntaxin. For the $\alpha_{1A}$ fusion proteins, no binding to GST alone was detected. Titration studies demonstrated that, under our binding conditions, half-maximal saturation occurs at approximately 2 $\mu$M concentration of hBI 722–1036. These results with the BI isoform of $\alpha_{1A}$ are in contrast to the binding studies with the N-type channel where the binding contribution of the two smaller fusion proteins rbB 718–859 and rbB 832–963 are additive (FIG. 14), and the affinity of the corresponding fusion protein (rbB 718–963) is approximately 10-fold greater (0.2 $\mu$M). It appears that the syntaxin-binding site on the BI isoform of $\alpha_{1A}$ has lower affinity than the one on the N-type channel and, therefore, requires the entire binding region to attain an active conformation.

Example 9

Figure 1:
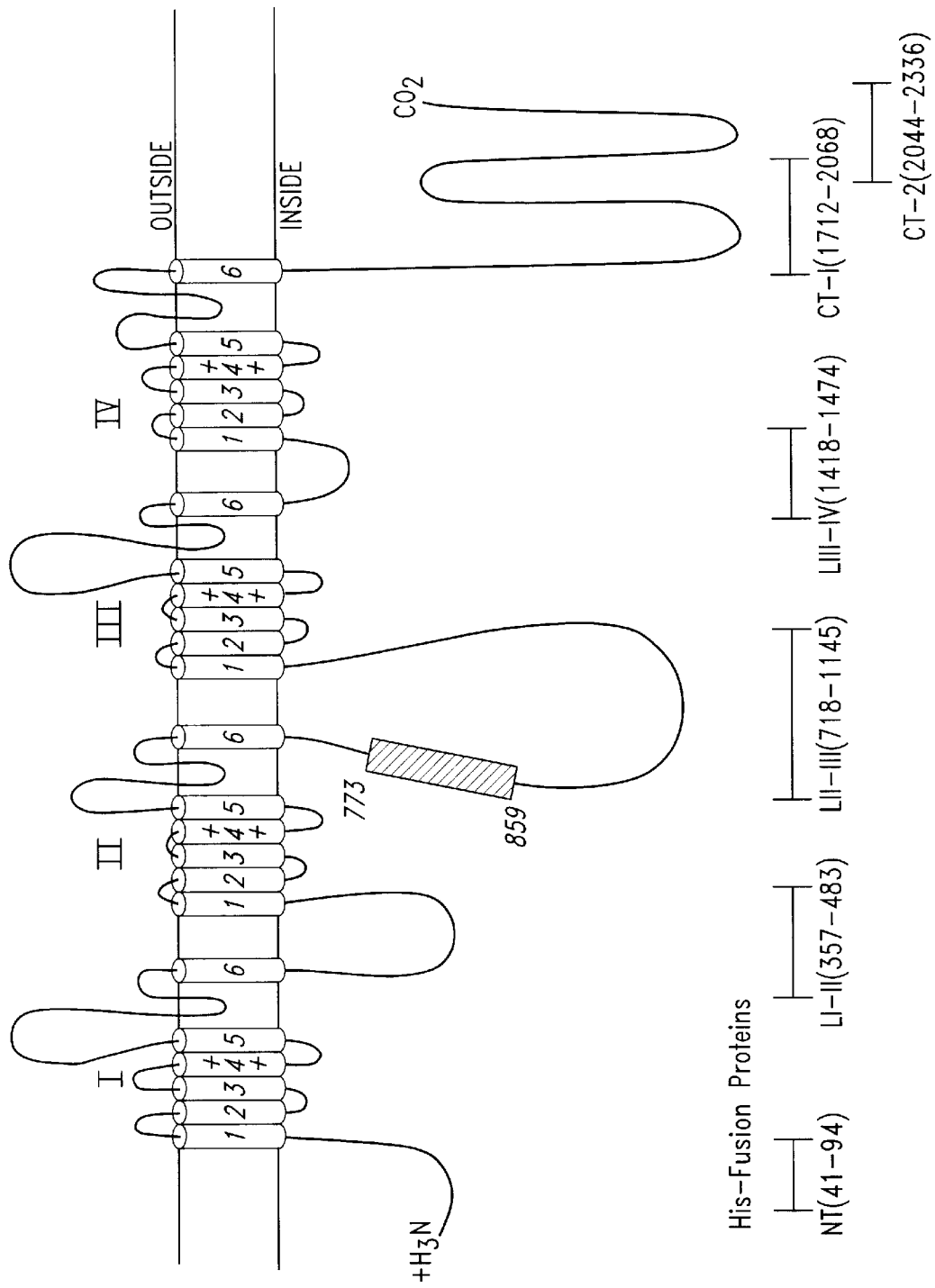
FIG. 1 is a drawing depicting the predicted topological structure of the α1 subunit of class B N-type calcium channels. The location of the recombinant His-fusion proteins of calcium channel cytoplasmic domains generated for binding studies are depicted. The filled-in rectangle indicates a region of interaction with syntaxin 1A.

Both $\alpha_{1A}$ and $\alpha_{1B}$ Bind to the C-Terminal One-Third of Syntaxin Syntaxin possesses three heptad repeats, two in its amino terminus (aa 30–64 and aa 68–112) and one in its carboxy terminus (aa 189–231) (Inoue et al., J. Biol. Chem. 267:10613–10619, 1992). As shown above, the rbB 718–859 fusion protein of a I B binds to a GST-syntaxin deletion construct which contained only the C-terminal one-third (aa 181–288) of syntaxin 1A. However, it remained possible that the second syntaxin-binding segment of $\alpha_{1B}$ (rbB 832–963, FIG. 1B) binds to another site on syntaxin, possibly the N-terminal heptad repeats. Binding studies with rbB 718–859, rbB 832–963 and rbB 718–963 fusion proteins of $\alpha_{1B}$ and the C-terminal segment of syntaxin were performed. As shown in FIG. 16, all three fusion proteins bind to the C-terminal one-third of syntaxin 1A (aa 181–288). Conversely, no binding to GST-syntaxin-NT (aa 2–190) or GST alone could be detected, suggesting that both of the syntaxin-binding regions of N-type Ca$^{++}$ channels interact with a C-terminal site on syntaxin near the intracellular surface of the presynaptic plasma membrane.

Similar to full-length syntaxin 1A, only the largest fusion protein of the BI isoform showed any detectable binding to syntaxin fragments. It binds specifically to the C-terminal one-third of syntaxin 1A (aa 181–288) whereas no binding to GST-syntaxin-NT or GST alone occurred.

Example 10

$\alpha_{1A}$ and $\alpha_{1B}$ Compete for the Same Binding Region on Syntaxin 1A Because both $\alpha_{1B}$ and the BI isoform of $\alpha_{1A}$ bound to the C-terminal one-third of syntaxin IA, it was investigated whether both occupy the same binding site on syntaxin. Competition assays were performed with fusion proteins of $\alpha_{1B}$ and the BI isoform of $\alpha_{1A}$ present simultaneously in the binding solution. GST-syntaxin 1A was bound to glutathione-Sepharose beads and incubated with a constant concentration (5 $\mu$M) of hBI 722–1036 of $\alpha_{1A}$ and increasing concentrations of rbB 718–963 of $\alpha_{1B}$. The signal intensity of hBI 722–1036 of the P/Q-type channel diminishes progressively while the signal intensity of rbB 718–963 of the N-type channel increases. These results demonstrate that P/Q-type and N-type channels indeed compete for the same binding region on syntaxin 1A.

Example 11

$\alpha_{1A}$ and $\alpha_{1B}$ Bind to the Presynaptic Protein SNAP-25

In order to elucidate whether the Ca$^{++}$ channels interact with SNAP-25 (another presynaptic plasma membrane protein), a GST fusion protein of SNAP-25 was constructed as described in Example 1. GST-SNAP-25 was bound to glutathione-Sepharose beads and incubated with equal concentrations of the three $\alpha_{1B}$ fusion proteins and the six rbA and hBI $\alpha_{1A}$ fusion proteins. No binding to GST alone was detected, demonstrating the specificity of the interactions. In contrast, GST-SNAP-25 interacts with $L_{II-III}$ of all three Ca$^{++}$ channel types (FIG. 17).

All three fusion proteins of the N-type channel (rbB 718–859, rbB 832–963, and rbB 718–963) bound to GST-SNAP-25. The signal intensities of rbB 718–859 and rbB 832–963 were comparable to the intensity of the rbB 718–963 signal. These data demonstrate that the same two adjacent regions on the N-type channel which bind to syntaxin are also able to bind to SNAP-25.

The hBI 722–1036 fusion protein of the P/Q-type Ca$^{++}$ channel shows the most intense immunoblot signal. Titration studies demonstrate half-maximal saturation at approximately 1–2 $\mu$M, comparable to that for syntaxin. The long exposure shown in FIG. 17 reveals weak binding of hBI 843–1036, whereas no binding of hBI 722–895 is observed. These data support the hypothesis that both regions of the binding site on the BI isoform of $\alpha_{1A}$ are required for high affinity binding of presynaptic proteins.

In contrast to the BI isoform, the rbA 724–981 fusion protein shows weak binding to GST-SNAP-25. Nevertheless, this binding is specific because no binding to GST alone is observed. In addition, a fusion protein containing the entire intracellular loop of the rbA binds with comparable intensity. Although the binding is much weaker than the corresponding region of the BI isoform, these data suggest that the rbA isoform of the P/Q-type channel can also interact with proteins of the docking and fusion machinery. Evidently, the sequence differences in $L_{II-III}$ between BI and rbA isoforms results in different binding affinities for SNAP-25.

Example 12

$\alpha_{1A}$ and $\alpha_{1B}$ Compete for the Same Binding Region on SNAP-25

In order to test if the binding regions on $\alpha_{1B}$ and the BI isoform of $\alpha_{1A}$ compete for binding to SNAP-25, a competition assay was performed with GST-SNAP-25 bound to glutathione-Sepharose beads. As shown in FIG. 18, increasing concentrations of rbB 718–963 of $\alpha_{1B}$ displace hBI 722–1036 of $\alpha_{1A}$ from its binding site on SNAP-25. Evidently, $\alpha_{1A}$ and $\alpha_{1B}$ interact with identical or overlapping regions on SNAP-25 as well as on syntaxin.

All publications and patent applications mentioned in this specification are herein incorporated by reference to the same extent as if each individual publication or patent application was specifically and individually incorporated by reference.

From the foregoing, it will be evident that, although specific embodiments of the invention have been described herein for purposes of illustration, various modifications may be made without deviating from the spirit and scope of the invention.

What is claimed is:

1. A method of screening for compounds that bind a presynaptic calcium channel peptide which is able to bind syntax or SNAP-25, comprising the steps of:

(a) contacting a presynaptic calcium channel peptide that is able to bind syntaxin or SNAP-25, or a presynaptic calcium channel peptide modified with one or more amino acid addition, deletion or substitution, with a non-antibody candidate compound under conditions sufficient to permit binding between the peptide and the candidate compound, wherein the modification does not affect the modified peptide's ability to bind syntaxin or SNAP-25 when compared to the unmodified presynaptic calcium channel peptide, wherein the peptide is not intact presynaptic calcium channel; and (b) detecting the presence or absence of binding between the peptide and the candidate compound, thereby determining whether the candidate compound bound to the peptide.

2. A method of screening for compounds that bind a presynaptic calcium channel peptide which is able to bind syntaxin or SNAP-25, comprising the steps of:

(a) contacting a peptide with a non-antibody candidate compound under conditions sufficient to permit binding between the peptide and the candidate compound, wherein the peptide is a peptide consisting of the amino acid sequence of FIG. 11B (SEQ ID NO:3) from glutamic acid, amino acid 717, to threonine, amino acid 1036, or is a peptide consisting of an amino acid sequence of between 246 and 427 amino acid residues in length wherein said amino acid sequence contains the amino acid sequences of FIG. 11B (SEQ ID NO:3) from glutamic acid, amino acid 717, to arginine, amino acid 962 or that sequence modified with one or more amino acid addition, deletion or substitution wherein the modification does not affect the modified peptide's ability to bind syntaxin or SNAP-25 when compared to the unmodified presynaptic calcium channel peptide, wherein the peptide is not intact presynaptic calcium channel; and (b) detecting the presence or absence of binding between the peptide and the candidate compound, thereby determining whether the candidate compound bound to the peptide.

* * * * *

UNITED STATES PATENT AND TRADEMARK OFFICE
CERTIFICATE OF CORRECTION

PATENT NO. : 6,090,631
DATED : July 18, 2000
INVENTOR(S) : Catterall and Sheng

It is certified that error appears in the above-identified patent and that said Letters Patent is hereby corrected as shown below:

Claim 1, Column 33,
Line 23, should read, -- syntaxin or SNAP-25 --.

Signed and Sealed this

Twenty-eighth Day of August, 2001

*Attest:*

NICHOLAS P. GODICI
*Attesting Officer*    *Acting Director of the United States Patent and Trademark Office*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 87 amino acids
      (B) TYPE: amino acid
      (C) STRANDEDNESS:
      (D) TOPOLOGY: linear (xi) SEQUENCE DESCRIPTION: SEQ ID NO:1:

```
Ala Ser Gln Leu Arg Leu Gln Asn Leu Arg Ala Ser Cys Glu Ala Leu
1               5                   10                  15

Tyr Ser Glu Met Asp Pro Glu Glu Arg Leu Arg Tyr Ala Ser Thr Arg
            20                  25                  30

Asn Val Arg Pro Asp Met Lys Thr His Met Asp Arg Pro Arg Val Val
        35                  40                  45

Glu Pro Gly Arg Asp Gly Leu Arg Gly Pro Ala Gly Asn Lys Ser Lys
    50                  55                  60

Pro Glu Gly Thr Glu Ala Thr Glu Gly Ala Asp Pro Pro Arg Arg His
65                  70                  75                  80

His Arg His Arg Asp Arg Asp
                85
```

(2) INFORMATION FOR SEQ ID NO:2:

(i) SEQUENCE CHARACTERISTICS:
      (A) LENGTH: 434 amino acids
      (B) TYPE: amino acid
      (C) STRANDEDNESS:
      (D) TOPOLOGY: linear (xi) SEQUENCE DESCRIPTION: SEQ ID NO:2:

```
Val Asp Asn Leu Ala Asn Ala Gln Glu Leu Thr Lys Asp Glu Glu Glu
1               5                   10                  15

Met Glu Glu Ala Ala Asn Gln Lys Leu Ala Leu Gln Lys Ala Lys Glu
            20                  25                  30

Val Ala Glu Val Ser Pro Met Ser Ala Ala Asn Ile Ser Ile Ala Ala
        35                  40                  45

Arg Gln Gln Asn Ser Ala Lys Ala Arg Ser Val Trp Glu Gln Arg Ala
    50                  55                  60

Ser Gln Leu Arg Leu Gln Asn Leu Arg Ala Ser Cys Glu Ala Leu Tyr
65                  70                  75                  80

Ser Glu Met Asp Pro Glu Glu Arg Leu Arg Tyr Ala Ser Thr Arg His
                85                  90                  95

Val Arg Pro Asp Met Lys Thr His Met Asp Arg Pro Leu Val Val Glu
            100                 105                 110

Pro Gly Arg Asp Gly Leu Arg Gly Pro Ala Gly Asn Lys Ser Lys Pro
        115                 120                 125

Glu Gly Thr Glu Ala Thr Glu Gly Ala Asp Pro Pro Arg Arg His His
    130                 135                 140

Arg His Arg Asp Arg Asp Lys Thr Ser Ala Ser Thr Pro Ala Gly Gly
145                 150                 155                 160

Glu Gln Asp Arg Thr Asp Cys Pro Lys Ala Glu Ser Thr Glu Thr Gly
                165                 170                 175
```

-continued

```
Ala Arg Glu Glu Arg Ala Arg Pro Arg Arg Ser His Ser Lys Glu Ala
            180                 185                 190

Pro Gly Ala Asp Thr Gln Val Arg Cys Glu Arg Ser Arg Arg His His
        195                 200                 205

Arg Arg Gly Ser Pro Glu Glu Ala Thr Glu Arg Glu Pro Arg Arg His
        210                 215                 220

Arg Ala His Arg His Ala Gln Asp Ser Ser Lys Gly Lys Glu Gly
225                 230                 235                 240

Thr Ala Pro Val Leu Val Pro Lys Gly Glu Arg Ala Arg His Arg
                245                 250                 255

Gly Pro Arg Thr Gly Pro Arg Glu Thr Glu Asn Ser Glu Glu Pro Thr
            260                 265                 270

Arg Arg His Arg Ala Lys His Lys Val Pro Pro Thr Leu Glu Pro Pro
            275                 280                 285

Glu Arg Glu Val Ala Glu Lys Glu Ser Asn Val Val Glu Gly Asp Lys
            290                 295                 300

Glu Thr Arg Asn His Gln Pro Lys Glu Pro Arg Cys Asp Leu Glu Ala
305                 310                 315                 320

Ile Ala Val Thr Gly Val Gly Ser Leu His Met Leu Pro Ser Thr Cys
                325                 330                 335

Leu Gln Lys Val Asp Glu Gln Pro Glu Asp Ala Asp Asn Gln Arg Asn
                340                 345                 350

Val Thr Arg Met Gly Ser Gln Pro Ser Asp Pro Ser Thr Thr Val His
            355                 360                 365

Val Pro Val Thr Leu Thr Gly Pro Pro Gly Glu Ala Thr Val Val Pro
370                 375                 380

Ser Ala Asn Thr Asp Leu Glu Gly Gln Ala Glu Gly Lys Lys Glu Ala
385                 390                 395                 400

Glu Ala Asp Asp Val Leu Arg Arg Gly Pro Arg Pro Ile Val Pro Tyr
                405                 410                 415

Ser Ser Met Phe Cys Leu Ser Pro Thr Asn Leu Leu Arg Arg Phe Cys
                420                 425                 430

His Tyr
```

(2) INFORMATION FOR SEQ ID NO:3:

(i) SEQUENCE CHARACTERISTICS:
        (A) LENGTH: 434 amino acids
        (B) TYPE: amino acid
        (C) STRANDEDNESS:
        (D) TOPOLOGY: linear (xi) SEQUENCE DESCRIPTION: SEQ ID NO:3:

```
Asp Asn Leu Ala Asn Ala Gln Glu Leu Thr Lys Asp Glu Glu Met
1               5                   10                  15

Glu Glu Ala Ala Asn Gln Lys Leu Ala Leu Gln Lys Ala Lys Glu Val
            20                  25                  30

Ala Glu Val Ser Pro Met Ser Ala Asn Ile Ser Ile Ala Ala Arg
        35                  40                  45

Gln Gln Asn Ser Ala Lys Ala Arg Ser Val Trp Glu Gln Arg Ala Ser
    50                  55                  60

Gln Leu Arg Leu Gln Asn Leu Arg Ala Ser Cys Glu Ala Leu Tyr Ser
65                  70                  75                  80

Glu Met Asp Pro Glu Glu Arg Leu Arg Phe Ala Thr Thr Arg His Leu
                85                  90                  95
```

```
Arg Pro Asp Met Lys Thr His Leu Asp Arg Pro Leu Val Val Glu Leu
                100                 105                 110

Gly Arg Asp Gly Ala Arg Gly Pro Val Gly Gly Lys Ala Arg Pro Glu
            115                 120                 125

Ala Ala Glu Ala Pro Glu Gly Val Asp Pro Pro Arg Arg His His Arg
        130                 135                 140

His Arg Asp Lys Asp Lys Thr Pro Ala Ala Gly Asp Gln Asp Arg Ala
145                 150                 155                 160

Glu Ala Pro Lys Ala Glu Ser Gly Glu Pro Gly Ala Arg Glu Glu Arg
                165                 170                 175

Pro Arg Pro His Arg Ser His Ser Lys Glu Ala Ala Gly Pro Pro Glu
            180                 185                 190

Ala Arg Ser Glu Arg Gly Arg Gly Pro Gly Pro Glu Gly Gly Arg Arg
        195                 200                 205

His His Arg Arg Gly Ser Pro Glu Glu Ala Ala Glu Arg Glu Pro Arg
210                 215                 220

Arg His Arg Ala His Arg His Gln Asp Pro Ser Lys Glu Cys Ala Gly
225                 230                 235                 240

Ala Lys Gly Glu Arg Arg Ala Arg His Arg Gly Gly Pro Arg Ala Gly
                245                 250                 255

Pro Arg Glu Ala Glu Ser Gly Glu Glu Pro Ala Arg Arg His Arg Ala
            260                 265                 270

Arg His Lys Ala Gln Pro Ala His Glu Ala Val Glu Lys Glu Thr Thr
        275                 280                 285

Glu Lys Glu Ala Thr Glu Lys Glu Ala Glu Ile Val Glu Ala Asp Lys
        290                 295                 300

Glu Lys Glu Leu Arg Asn His Gln Pro Arg Glu Pro His Cys Asp Leu
305                 310                 315                 320

Glu Thr Ser Gly Thr Val Thr Val Gly Pro Met His Thr Leu Pro Ser
                325                 330                 335

Thr Cys Leu Gln Lys Val Glu Gln Pro Glu Asp Ala Asp Asn Gln
            340                 345                 350

Arg Asn Val Thr Arg Met Gly Ser Gln Pro Pro Asp Pro Asn Thr Ile
        355                 360                 365

Val His Ile Pro Val Met Leu Thr Gly Pro Leu Gly Glu Ala Thr Val
370                 375                 380

Val Pro Ser Gly Asn Val Asp Leu Glu Ser Gln Ala Glu Gly Lys Lys
385                 390                 395                 400

Glu Val Glu Ala Asp Asp Val Met Arg Ser Gly Pro Arg Pro Ile Val
                405                 410                 415

Pro Tyr Ser Ser Met Phe Cys Leu Ser Pro Thr Asn Leu Leu Arg Arg
            420                 425                 430

Phe Cys (2) INFORMATION FOR SEQ ID NO:4:

(i) SEQUENCE CHARACTERISTICS:
        (A) LENGTH: 288 amino acids
        (B) TYPE: amino acid
        (C) STRANDEDNESS:
        (D) TOPOLOGY: linear (xi) SEQUENCE DESCRIPTION: SEQ ID NO:4:

Met Lys Asp Arg Thr Gln Glu Leu Arg Thr Ala Lys Asp Ser Asp Asp
1               5                   10                  15
```

```
Asp Asp Asp Val Thr Val Thr Val Asp Arg Asp Arg Phe Met Asp Glu
            20              25              30

Phe Phe Glu Gln Val Glu Glu Ile Arg Gly Phe Ile Asp Lys Ile Ala
        35              40                  45

Glu Asn Val Glu Glu Val Lys Arg Lys His Ser Ala Ile Leu Ala Ser
    50              55              60

Pro Asn Pro Asp Glu Lys Thr Lys Glu Glu Leu Glu Leu Met Ser
65              70              75              80

Asp Ile Lys Lys Thr Ala Asn Lys Val Arg Ser Lys Leu Lys Ser Ile
                85              90              95

Glu Gln Ser Ile Glu Gln Glu Glu Gly Leu Asn Arg Ser Ser Ala Asp
            100             105             110

Leu Arg Ile Arg Lys Thr Gln His Ser Thr Leu Ser Arg Lys Phe Val
        115             120             125

Glu Val Met Ser Glu Tyr Asn Ala Thr Gln Ser Asp Tyr Arg Glu Arg
        130             135             140

Cys Lys Gly Arg Ile Gln Arg Gln Leu Glu Ile Thr Gly Arg Thr Thr
145             150             155             160

Thr Ser Glu Glu Leu Glu Asp Met Leu Glu Ser Gly Asn Pro Ala Ile
            165             170             175

Phe Ala Ser Gly Ile Ile Met Asp Ser Ser Ile Ser Lys Gln Ala Leu
            180             185             190

Ser Glu Ile Glu Thr Arg His Ser Glu Ile Ile Lys Leu Glu Asn Ser
            195             200             205

Ile Arg Glu Leu His Asp Met Phe Met Asp Met Ala Met Leu Val Glu
            210             215             220

Ser Gln Gly Glu Met Ile Asp Arg Ile Glu Tyr Asn Val Glu His Ala
225             230             235             240

Val Asp Tyr Val Glu Arg Ala Val Ser Asp Thr Lys Lys Ala Val Lys
            245             250             255

Tyr Gln Ser Lys Ala Arg Arg Lys Lys Ile Met Ile Ile Ile Cys Cys
            260             265             270

Val Ile Leu Gly Ile Ile Ile Ala Ser Thr Ile Gly Gly Ile Phe Gly
            275             280             285

(2) INFORMATION FOR SEQ ID NO:5:

(i) SEQUENCE CHARACTERISTICS:
        (A) LENGTH: 315 amino acids
        (B) TYPE: amino acid
        (C) STRANDEDNESS:
        (D) TOPOLOGY: linear (xi) SEQUENCE DESCRIPTION: SEQ ID NO:5:

Glu Leu Thr Lys Asp Glu Gln Glu Glu Glu Ala Val Asn Gln Lys
1               5               10              15

Leu Ala Leu Gln Lys Ala Lys Gln Val Ala Glu Val Ser Pro Leu Ser
            20              25              30

Ala Ala Asn Met Ser Ile Ala Met Lys Glu Gln Gln Lys Asn Gln Lys
        35              40                  45

Pro Ala Lys Ser Val Trp Glu Gln Arg Thr Ser Glu Met Arg Lys Gln
    50              55              60

Asn Leu Leu Ala Ser Arg Glu Ala Leu Tyr Ser Glu Met Asp Pro Glu
65              70              75              80

Glu Arg Trp Lys Ala Ser Tyr Ala Arg His Leu Arg Pro Asp Met Lys
```

```
                    85                  90                  95
Thr His Leu Asp Arg Pro Leu Val Val Asp Pro Gln Glu Asn Arg Asn
                    100                 105                 110

Asn Asn Thr Asn Lys Ser Arg Val Ala Glu Pro Thr Val Asp Gln Arg
                    115                 120                 125

Leu Gly Gln Gln Arg Ala Glu Asp Phe Leu Arg Lys Gln Ala Arg His
130                 135                 140

His Asp Arg Ala Arg Asp Pro Ser Ala His Ala Ala Gly Leu Asp
145                 150                 155                 160

Ala Arg Arg Pro Trp Ala Gly Ser Gln Glu Ala Glu Leu Ser Arg Glu
                    165                 170                 175

Gly Pro Tyr Gly Arg Glu Ser Asp His Gln Ala Arg Glu Gly Gly Leu
                    180                 185                 190

Glu Pro Pro Gly Phe Trp Glu Gly Glu Ala Glu Arg Gly Lys Ala Gly
                    195                 200                 205

Asp Pro His Arg Arg His Ala His Arg Gln Gly Val Gly Gly Ser Gly
                    210                 215                 220

Gly Ser Arg Ser Gly Ser Pro Arg Thr Gly Thr Ala Asp Gly Glu Pro
225                 230                 235                 240

Arg Arg His Arg Val His Arg Arg Pro Gly Glu Asp Gly Pro Asp Asp
                    245                 250                 255

Lys Ala Glu Arg Arg Gly Arg His Arg Glu Gly Ser Arg Pro Ala Arg
                    260                 265                 270

Ser Gly Glu Gly Glu Ala Glu Gly Pro Asp Gly Gly Gly Gly Gly
                    275                 280                 285

Gly Glu Arg Arg Arg His Arg His Gly Pro Pro Pro Ala Tyr Asp
290                 295                 300

Pro Asp Ala Arg Arg Asp Asp Arg Glu Arg Arg
305                 310                 315

(2) INFORMATION FOR SEQ ID NO:6:

(i) SEQUENCE CHARACTERISTICS:
        (A) LENGTH: 305 amino acids
        (B) TYPE: amino acid
        (C) STRANDEDNESS:
        (D) TOPOLOGY: linear (xi) SEQUENCE DESCRIPTION: SEQ ID NO:6:

Glu Leu Thr Lys Asp Glu Gln Glu Glu Glu Ala Ala Asn Gln Lys
1               5                   10                  15

Leu Ala Leu Gln Lys Ala Lys Glu Val Ala Glu Val Ser Pro Leu Ser
                    20                  25                  30

Ala Ala Asn Met Ser Ile Ala Val Lys Glu Gln Gln Lys Asn Gln Lys
                    35                  40                  45

Pro Ala Lys Ser Val Trp Glu Gln Arg Thr Ser Glu Met Arg Lys Gln
                    50                  55                  60

Asn Leu Leu Ala Ser Arg Glu Ala Leu Tyr Asn Glu Met Asp Pro Asp
65                  70                  75                  80

Glu Arg Trp Lys Ala Ala Tyr Thr Arg His Leu Arg Pro Asp Met Lys
                    85                  90                  95

Thr His Leu Asp Arg Pro Leu Val Val Asp Pro Gln Glu Asn Arg Asn
                    100                 105                 110

Asn Asn Thr Asn Lys Ser Arg Ala Ala Glu Pro Thr Val Asp Gln Arg
                    115                 120                 125
```

```
Leu Gly Gln Gln Arg Ala Glu Asp Phe Leu Arg Lys Gln Ala Arg Tyr
    130                 135                 140

His Asp Arg Ala Arg Asp Pro Ser Gly Ser Ala Gly Leu Asp Ala Arg
145                 150                 155                 160

Arg Pro Trp Ala Gly Ser Gln Glu Ala Glu Leu Ser Arg Glu Gly Pro
                165                 170                 175

Tyr Gly Arg Glu Ser Asp His His Ala Arg Glu Gly Ser Leu Glu Gln
            180                 185                 190

Pro Gly Phe Trp Glu Gly Glu Ala Glu Arg Gly Lys Ala Gly Asp Pro
        195                 200                 205

His Arg Arg His Val His Arg Gln Gly Gly Ser Arg Glu Ser Arg Ser
210                 215                 220

Gly Ser Pro Arg Thr Gly Ala Asp Gly Glu His Arg Arg His Arg Ala
225                 230                 235                 240

His Arg Arg Pro Gly Glu Glu Gly Pro Glu Asp Lys Ala Glu Arg Arg
                245                 250                 255

Ala Arg His Arg Glu Gly Ser Arg Pro Ala Arg Gly Gly Glu Gly Glu
            260                 265                 270

Gly Glu Gly Pro Asp Gly Gly Glu Arg Arg Arg His Arg His Gly
        275                 280                 285

Ala Pro Ala Thr Tyr Glu Gly Asp Ala Arg Arg Glu Asp Lys Glu Arg
    290                 295                 300

Arg
305

(2) INFORMATION FOR SEQ ID NO:7:

(i) SEQUENCE CHARACTERISTICS:
        (A) LENGTH: 260 amino acids
        (B) TYPE: amino acid
        (C) STRANDEDNESS:
        (D) TOPOLOGY: linear (xi) SEQUENCE DESCRIPTION: SEQ ID NO:7:

Glu Leu Thr Lys Asp Glu Gln Glu Glu Glu Ala Ala Asn Gln Lys
1               5                   10                  15

Leu Ala Leu Gln Lys Ala Lys Glu Val Ala Glu Val Ser Pro Leu Ser
                20                  25                  30

Ala Ala Asn Met Ser Ile Ala Val Lys Glu Gln Gln Lys Asn Gln Lys
            35                  40                  45

Pro Ala Lys Ser Val Trp Glu Gln Arg Thr Ser Glu Met Arg Lys Gln
    50                  55                  60

Asn Leu Leu Ala Ser Arg Glu Ala Leu Tyr Gly Asp Ala Ala Glu Arg
65                  70                  75                  80

Trp Pro Thr Thr Tyr Ala Arg Pro Leu Arg Pro Asp Val Lys Thr His
                85                  90                  95

Leu Asp Arg Pro Leu Val Val Asp Pro Gln Glu Asn Arg Asn Asn Asn
                100                 105                 110

Thr Asn Lys Ser Arg Ala Pro Glu Ala Leu Arg Gln Thr Ala Arg Pro
            115                 120                 125

Arg Glu Ser Ala Arg Asp Pro Asp Ala Arg Arg Ala Trp Pro Ser Ser
        130                 135                 140

Pro Glu Arg Ala Pro Gly Arg Glu Gly Pro Tyr Gly Arg Glu Ser Glu
145                 150                 155                 160

Pro Gln Gln Arg Glu His Ala Pro Pro Arg Glu His Val Pro Trp Asp
                165                 170                 175
```

```
Ala Asp Pro Glu Arg Ala Lys Ala Gly Asp Ala Pro Arg Arg His Thr
            180                 185                 190

His Arg Pro Val Ala Glu Gly Glu Pro Arg Arg His Arg Ala Arg Arg
        195                 200                 205

Arg Pro Gly Asp Glu Pro Asp Asp Arg Pro Glu Arg Arg Pro Arg Pro
        210             215             220

Arg Asp Ala Thr Arg Pro Ala Arg Ala Ala Asp Gly Glu Gly Asp Asp
225             230             235                     240

Gly Glu Arg Lys Arg Arg His Arg His Gly Pro Pro Ala His Asp Asp
            245             250                     255

Arg Glu Arg Arg
            260
```